United States Patent
Murata et al.

Patent Number: 5,194,624
Date of Patent: Mar. 16, 1993

[54] INTERMEDIATES FOR THE PREPARATION OF COMPOUNDS OF ANTIMICROBIAL ACTIVITY

[75] Inventors: Masayoshi Murata, Osaka; Hideo Tsutumi, Toyonaka; Keiji Matsuda, Takatsuki; Kohji Hattori, Sakai; Takashi Nakajima, Toyonaka, all of Japan

[73] Assignee: Fujisawa Pharmaceutical Co., Ltd., Osaka, Japan

[21] Appl. No.: 520,814

[22] Filed: May 9, 1990

Related U.S. Application Data

[62] Division of Ser. No. 347,579, May 5, 1989, Pat. No. 4,963,544.

[30] Foreign Application Priority Data

May 23, 1988 [GB] United Kingdom ............ 8812160
Mar. 22, 1989 [GB] United Kingdom ............ 8906576

[51] Int. Cl.$^5$ .................. C07D 487/04; C07D 403/06
[52] U.S. Cl. .................. 548/314.7; 548/364.1; 546/281
[58] Field of Search ............ 548/336, 348, 374, 318; 546/281

[56] References Cited

U.S. PATENT DOCUMENTS 4,241,060 12/1980 Smithen .................. 548/336
4,746,736 5/1988 Kim .................. 540/350

*Primary Examiner*—Mary C. Lee
*Assistant Examiner*—Lenora A. Miltenberger
*Attorney, Agent, or Firm*—Oblon, Spivak, McClelland, Maier & Neustadt

[57] ABSTRACT

The invention relates to compounds of the formula:

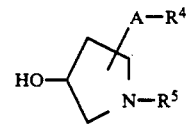

the formula:

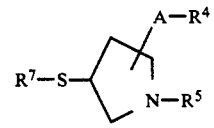

or the formula:

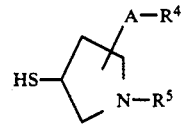

in which
  $R^4$ is an unsaturated, 5 or 6-membered heteromonocyclic group,
  $R^5$ is hydrogen, lower alkanimidoyl or imino-protective group,
  $R^7$ is ar(lower)alkyl or acyl derived from a carboxylic, carbonic, sulfonic or carbamic acid, and
  A is lower alkylene,
or a salt thereof, useful as intermediates in the preparation of antimicrobial agents.

6 Claims, No Drawings

INTERMEDIATES FOR THE PREPARATION OF COMPOUNDS OF ANTIMICROBIAL ACTIVITY

This is a division of application Ser. No. 07/347,579, filed on May 5, 1989, now U.S. Pat. No. 4,963,544.

The present invention relates to novel 3-pyrrolidinylthio-1-azabicyclo[3.2.0]hept-2-ene-2-carboxylic acid compounds and pharmaceutically acceptable salts thereof.

More particularly, it relates to novel 3-pyrrolidinylthio-1-azabicyclo[3.2.0]hept-2-ene-2-carboxylic acid compounds and pharmaceutically acceptable salts thereof, which have antimicrobial activity to processes for the preparation thereof, to a pharmaceutical composition comprising the same, and to a use of the same as a medicament and in the treatment of infectious diseases in human being or animal.

Accordingly, one object of the present invention is to provide novel 3-pyrrolidinylthio-1-azabicyclo[3.2.0]hept-2-ene-2-carboxylic acid compounds and pharmaceutically acceptable salts thereof, which are highly active against a number of pathogenic microorganisms and are useful as antimicrobial agents.

Another object of the present invention is to provide processes for the preparation of novel 3-pyrrolidinylthio-1-azabicyclo[3.2.0]hept-2-ene-2-carboxylic acid compounds and salts thereof.

A further object of the present invention is to provide a pharmaceutical composition comprising, as an active ingredient, said 3-pyrrolidinylthio-1-azabicyclo[3.2.0]hept-2-ene-2-carboxylic acid compounds and pharmaceutically acceptable salts thereof.

Still further object of the present invention is to provide a use of said 3-pyrrolidinylthio-1-azabicyclo[3.2.0]hept-2-ene-2-carboxylic acid compounds and pharmaceutically acceptable salts thereof as a medicament and in the treatment of infectious diseases by pathogenic microorganisms in human being or animal.

The object 3-pyrrolidinylthio-1-azabicyclo[3.2.0]hept-2-ene-2-carboxylic acid compounds are novel and can be represented by the following general formula:

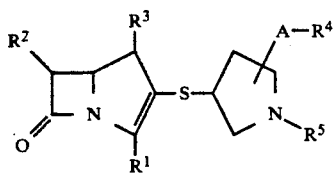

(I)

in which
$R^1$ is carboxy or protected carboxy,
$R^2$ is hydroxy(lower)alkyl or protected hydroxy(lower)alkyl,
$R^3$ is hydrogen or lower alkyl,
$R^4$ is unsaturated heterocyclic group which may be substituted by suitable substituent(s),
$R^5$ is hydrogen, lower alkanimidoyl or imino-protective group, and
A is lower alkylene,
and pharmaceutically acceptable salts thereof.

Suitable pharmaceutically acceptable salts of the object compound (I) are conventional non-toxic salts and may include a salt with a base such as an inorganic base salt, for example, an alkali metal salt (e.g. sodium salt, potassium salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, etc.); a salt with an acid such as inorganic acid addition salt (e.g. hydrochloride, hydrobromide, sulfate, phosphate, etc.), an organic acid addition salt (e.g. formate, acetate, trifluoroacetate, maleate, tartrate, methanesulfonate, benzenesulfonate, etc.); a salt with a basic or acidic amino acid (e.g. arginine, aspartic acid, glutamic acid, etc.); an intermolecular or intramolecular quarternary salt; and the like.

The said intermolecular quarternary salt can be formed in case that the unsaturated heterocyclic group in $R^4$ in the compound (I) contains tertiary nitrogen atom (e.g. imidazolyl, pyrazolyl, 4-imidazolin-1-yl, etc.), and suitable intermolecular quaternary salt may include 1- and/or 3-substituted-1-imidazolio (lower)alkylsulfate such as 1- and/or 3-(lower)alkyl-1-imidazolio (lower)alkylsulfate (e.g. 3-methyl-1-imidazolio methylsulfate, 3-ethyl-1-imidazolio ethylsulfate, etc.), 1- and/or 3-carbamoyl(lower)alkyl-1-imidazolio (lower)alkylsulfate (e.g. 3-carbamoylmethyl-1-imidazolio methylsulfate, etc.), 1-and/or 3-(lower)alkanoyl(lower)alkyl-1-imidazolio (lower)alkylsulfate (e.g. 3-acetonyl-1-imidazolio methylsulfate, etc.), 1- and/or 3-phenyl(or nitrophenyl)(lower)alkoxycarbonyl(lower)alkyl-1-imidazolio (lower)alkylsulfate (e.g. 3-(4-nitrobenzyloxycarbonylmethyl)-1-imidazolio methylsulfate, etc.); 1- and/or 3-substituted-1-imidazolio halide such as 1- and/or 3-(lower)alkyl-1-imidazolio halide (e.g. 3-methyl-1-imidazolio iodide, 3-methyl-1-imidazolio chloride, 3-ethyl-1-imidazolio iodide, etc.), 3-carbamoyl(lower)alkyl-1-imidazolio halide (e.g. 3-carbamoylmethyl-1-imidazolio iodide, etc.), 3-(lower)alkanoyl(lower)alkyl-1-imidazolio halide (e.g. 3-acetonyl-1-imidazolio bromide, etc.), 3-phenyl(or nitrophenyl)(lower)alkoxycarbonyl(lower)alkyl-1-imidazolio halide [e.g. 3-(4-nitrobenzyloxycarbonylmethyl-1-imidazolio bromide, etc.]; and the like.

The said intramolecular salt can be formed in case that the unsaturated heterocyclic group in $R^4$ in the compound (I) contains tertiary nitrogen atom (e.g. imidazolyl, pyrazolyl, 4-imidazolin-1-yl, etc.) and $R^1$ is carboxy, and suitable intramolecular salt may include 1- and/or 3-substituted-1-imidazolio carboxylate such as 1-and/or 3-(lower)alkyl-1-imidazolio carboxylate (e.g. 3-methyl-1-imidazolio carboxylate, 3-ethyl-1-imidazolio carboxylate, 3-propyl-1-imidazolio carboxylate, 3-isopropyl-1-imidazolio carboxylate, 3-butyl-1-imidazolio carboxylate, etc.), 3-carbamoyl(lower)alkyl-1-imidazolio carboxylate (e.g. 3-carbamoylmethyl-1-imidazolio carboxylate, 3-carbamoylethyl-1-imidazolio carboxylate, 3-carbamoylpropyl-1-imidazolio carboxylate, 3-carbamoylbutyl-1-imidazolio carboxylate, etc.), 3-(lower)alkanoyl(lower)alkyl-1-imidazolio carboxylate (e.g. 3-acetonyl-1-imidazolio carboxylate, 3-propionylmethyl-1-imidazolio carboxylate, 3-butyrylmethyl-1-imidazolio carboxylate, 3-acetylethyl-1-imidazolio carboxylate, 3-acetylpropyl-1-imidazolio carboxylate, 3-acetylbutyl-1-imidazolio carboxylate, etc.), 3-phenyl(or nitrophenyl)(lower)alkoxycarbonyl(lower)alkyl-1-imidazolio carboxylate [e.g. 3-(4-nitrobenzyloxycarbonylmethyl)-1-imidazolio carboxylate, 3-(4-nitrobenzyloxycarbonylethyl)-1-imidazolio carboxylate, 3-(4-nitrobenzyloxycarbonylpropyl)-1-imidazolio carboxylate, 3-(4-nitrobenzyloxycarbonylbutyl)-1-imidazolio carboxylate, etc.], 3-carboxy(lower)alkyl-1-imidazolio carboxylate (e.g. 3-carboxymethyl-1-imidazolio carboxylate, etc.), and the like.

In the object compound (I) and the intermediary compounds mentioned below, it is to be understood that there may be one or more stereo-isomeric pair(s) such as optical isomers due to asymmetric carbon atom(s), and such isomers are also included within the scope of the present invention.

According to the present invention, the object compound (I) or pharmaceutically acceptable salts thereof can be prepared by the processes as illustrated by the following reaction schemes.

Process 1:

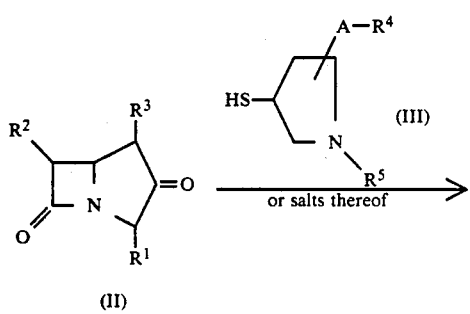

(II)
or a reactive derivative
at the oxo group thereof
or salts thereof (I)
or salts thereof Process 2:

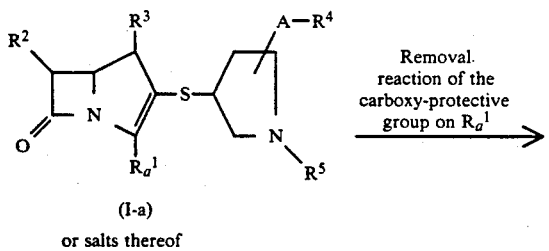

(I-a)
or salts thereof (I-b)
or salts thereof

Process 3:

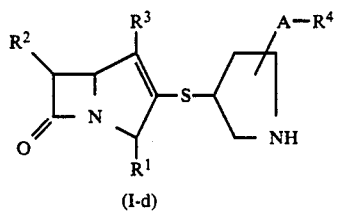

(I-c)
or salts thereof

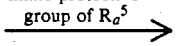 Removal reaction of the imino-protective group of $R_a^5$ (I-d)
or salts thereof Process 4:

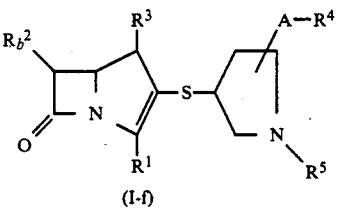

(I-e)
or salts thereof

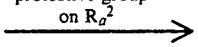 Removal reaction of the hydroxy-protective group on $R_a^2$ (I-f)
or salts thereof Process 5:

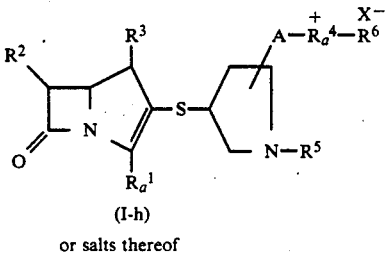

(I-g)
or salts thereof

 $R^6-X$ (IV)

(I-h)
or salts thereof

Process 6:

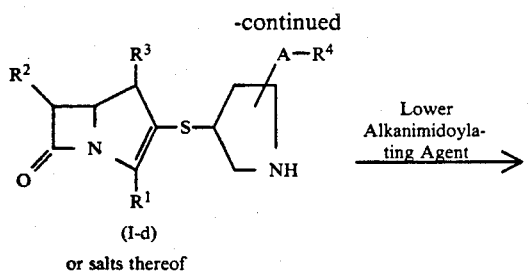

(I-d) or salts thereof

Lower Alkanimidoylating Agent →

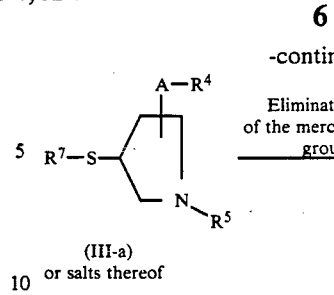

(III-a) or salts thereof

Elimination reaction of the mercaptoprotective group of $R^7$ →

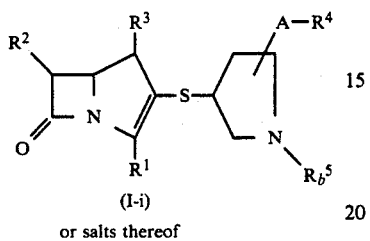

(I-i) or salts thereof

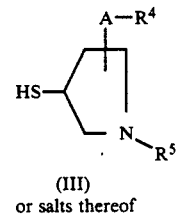

(III) or salts thereof in which $R^1$, $R^2$, $R^3$, $R^4$, $R^5$ and A are each as defined above, $R^1_a$ is protected carboxy, $R^2_a$ is protected hydroxy(lower)alkyl, $R^2_b$ is hydroxy(lower)alkyl, $R^4_a$ is unsaturated heterocyclic group containing tertiary nitrogen atom, which may be substituted by suitable substituent(s), $R_a^{+4}$ is unsaturated heterocyclic group containing quaternary nitrogen atom, which may be substituted by suitable substituent(s), $R^5_a$ is imino-protective group, $R^5_b$ is lower alkanimidoyl, $R^6$ is lower alkyl optionally substituted by a group consisting of carboxy and acyl, and X is an acid residue.

The compound (III) used in the Process 1 is new and can be prepared, for example, by the following methods or a conventional manner.

Method A:

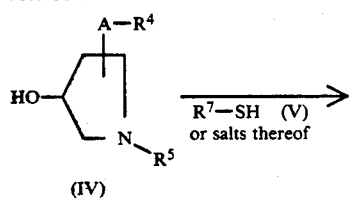

(IV) or a reactive derivative at the hydroxy group thereof or salts thereof $R^7$—SH  (V) or salts thereof →

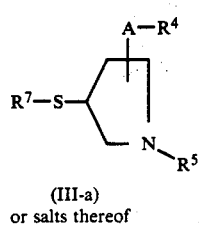

(III-a) or salts thereof

Method B:

In the above and subsequent descriptions of the present specification, suitable examples and illustrations of the various definitions which the present invention includes within the scope thereof are explained in detail as follows.

The term "lower" is intended to mean 1 to 6 carbon atom(s), unless otherwise indicated.

Suitable "protected carboxy" may include esterified carboxy wherein "esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, t-butyl ester, pentyl ester, hexyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, 1-(or 2- or 3- or 4-)acetoxybutyl ester, 1-(or 2-)propionyloxyethyl ester, 1-(or 2- or 3-)propionyloxypropyl ester, 1-(or 2-)butyryloxyethyl ester, 1-(or 2-)isobutyryloxyethyl ester, 1-(or 2-)pyvaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-)pentanoyloxyethyl ester, etc.], lower alkanesulfonyl(lower)alkyl ester (e.g. 2-mesylethyl ester, etc.), mono(or di or tri) halo(lower)alkyl ester (e.g. 2-iodoethyl ester, 2,2,2-trichloroethyl ester, etc.); lower alkoxycarbonyloxy(lower)alkyl ester [e.g. methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-) isopropoxycarbonyloxyethyl ester, etc.], phthalidylidene(lower)alkyl ester, or (5-lower alkyl-2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t- butylbenzyl ester, etc.); aryl ester which may have at least one suitable substituent(s) (e.g. phenyl ester, 4-chlorophenyl ester, tolyl ester, t-butylphenyl ester, xylyl ester, mesityl ester, cumenyl ester, etc.); phthalidyl ester; and the like.

More preferable example of the protected carboxy thus defined may be $C_2$-$C_4$ alkenyloxycarbonyl and phenyl( or nitrophenyl) ($C_1$-$C_4$)alkoxycarbonyl, and the most preferable one may be 4-nitrobenzyloxycarbonyl.

Suitable "hydroxy(lower)alkyl" may include straight or branched lower alkyl having hydroxy group such as hydroxymethyl, hydroxyethyl, hydroxypropyl, 1-(hydroxymethyl)ethyl, 1-hydroxy-1-methylethyl, hydroxybutyl, hydroxypentyl, hydroxyhexyl, and the like, in which more preferable example may be hydroxy($C_1$-$C_4$)alkyl and the most preferable one may be 1-hydroxyethyl.

Suitable "protected hydroxy(lower)alkyl" means aforementioned hydroxy(lower)alkyl, in which the hydroxy group is protected by a conventional hydroxy-protective group such as those mentioned in the explanation of imino-protective group as mentioned below; ar(lower)alkyl such as mono- or di- or triphenyl(lower)alkyl (e.g. benzyl, benzhydryl, trityl, etc.), etc.; trisubstituted silyl such as tri(lower)alkylsilyl (e.g. trimethylsilyl, triethylsilyl, isopropyldimethylsilyl, t-butyldimethylsilyl, diisopropylmethylsilyl, etc.), triarylsilyl (e.g. triphenylsilyl, etc.), triar(lower)alkylsilyl (e.g. tribenzylsilyl, etc.), etc.; and the like.

More preferable example of "protected hydroxy(lower)alkyl" thus defined may be [phenyl(or nitrophenyl)($C_1$-$C_4$)alkoxy]carbonyloxy($C_1$-$C_4$)alkyl and [tri($C_1$-$C_4$)alkylsilyl]oxy($C_1$-$C_4$)alkyl.

Suitable "lower alkyl" may include straight or branched one such as methyl, ethyl, propyl, isopropyl, butyl, t-butyl, pentyl, hexyl, and the like, in which more preferable example may be $C_1$-$C_4$ alkyl and the most preferable one may be methyl.

Suitable unsaturated heterocyclic group moiety of "unsaturated heterocyclic group which may be substituted by suitable substituent(s)", may include unsaturated monocyclic or polycyclic heterocyclic group containing at least one hetero-atom such as oxygen, sulfur or nitrogen atom.

Preferable unsaturated heterocyclic group may be unsaturated 3 to 8-membered, more preferably 5 or 6-membered, heteromonocyclic group containing 1 to 4 nitrogen atom(s), for example, pyrrolyl, pyrrolinyl, imidazolyl, imidazolinyl (e.g. 2-imidazolinyl, etc.), pyrazolyl, pyrazolinyl, pyridyl, pyridyl N-oxide, pyridinio, dihydropyridyl, tetrahydropyridyl [e.g. 1,2,3,6-tetrahydropyridyl, etc.], pyrimidinyl, pyrimidinio, pyrazinyl, pyrazinio, pyridazinyl, pyridazinio, triazinyl [e.g. 1,3,5-triazinyl, 1,2,4-triazinyl and 1,2,3-triazinyl], tetrahydrotriazinyl [e.g. 1,2,5,6-tetrahydro-1,2,4-triazinyl, 1,4,5,6-tetrahydro-1,2,4-triazinyl, etc.], triazinio, triazolyl [e.g. 1H-1,2,4-triazolyl, 1H-1,2,3-triazolyl, 2H-1,2,3-triazolyl, etc.], triazolio, tetrazinyl, tetrazinio, tetrazolyl [e.g. 1H-tetrazolyl and 2H-tetrazolyl], tetrazolio, etc.;

unsaturated 3 to 8-membered, more preferably 5 or 6-membered, heteromonocyclic group containing 1 to 2 oxygen tom(s) and 1 to 3 nitrogen atom(s), for example, oxazolyl, isoxazolyl, oxadiazolyl, (e.g. 1,2,4-oxadiazolyl, 1,3,4-oxadiazolyl, 1,2,5-oxadiazolyl, etc.), etc.;

unsaturated 3 to 8-membered, more preferably 5 or 6-membered, heteromonocyclic group containing 1 to 2 sulfur atom(s) and 1 to 3 nitrogen atom(s), for example, 1,3-thiazolyl, 1,2-thiazolyl, thiazolinyl, thiadiazolyl (e.g. 1,2,4-thiadiazolyl, 1,3,4-thiadiazolyl, 1,2,5-thiadiazolyl, 1,2,3-thiadiazolyl), etc.;

unsaturated 3 to 8-membered, more preferably 5 or 6-membered, heteromonocyclic group containing a sulfur atom, for example, thienyl, etc.; and the like, wherein said heterocyclic group may be substituted by one or more, preferably one to three suitable substituent(s) such as oxo; carboxy(lower)alkyl-, which is the aforementioned lower alkyl group substituted by carboxy; protected carboxy(lower)alkyl, which is the carboxy(lower)alkyl as mentioned above, in which the carboxy group is protected by a suitable carboxy-protective group to form so-called "esterified carboxy" as mentioned above; amino; protected amino in which the amino-protective group may be the same as those for the imino-protective group as mentioned below; lower alkylamino (e.g. methylamino, ethylamino, propylamino, isopropylamino, butylamino, hexylamino, etc.); ureido(lower)alkyl (e.g. ureidomethyl, ureidoethyl, ureidopropyl, ureidohexyl, etc.); carbamoyl; carbamoyl(lower)alkyl (e.g. carbamoylmethyl, etc.); lower alkyl as mentioned above; lower alkanoyl(lower)alkyl (e.g. acetylmethyl, etc.); amino(lower)alkyl (e.g. aminomethyl, aminoethyl, aminopropyl, aminobutyl, aminohexyl, etc.); protected amino(lower)alkyl, which is the amino(lower)alkyl group as mentioned above, in which the amino group is protected by a conventional amino-protective group such as those for the imino-protective group as mentioned below; hydroxy(lower)alkyl and protected hydroxy(lower)alkyl as mentioned above; azido(lower)alkyl (e.g. azidomethyl, azidoethyl, azidopropyl, azidohexyl, etc.); halo(lower)alkyl (e.g. chloromethyl, bromomethyl, iodoethyl, bromopropyl, bromohexyl, etc.); and the like. And further in case that said heterocyclic group is imidazolyl, pyrazolyl or imidazolinyl, the imino-moiety(ies) thereof may be protected by conventional imino-protective group(s) as mentioned below.

Preferable example of unsaturated heterocyclic group which may be substituted by suitable substituent(s) may be:

imidazolyl (e.g. imidazol-1-yl, etc.);

pyrazolyl (e.g. pyrazol-1-yl, etc.);

imidazolinyl (e.g. 4-imidazolin-1-yl, etc.);

oxoimidazolinyl (e.g. 2-oxo-4-imidazolin-1-yl, etc.).

Suitable "unsaturated heterocyclic group containing tertiary nitrogen atom, which may be substituted by suitable substituent(s)" may include unsaturated, monocyclic or polycyclic heterocyclic group containing tertiary nitrogen atom and/or other hetero-atom(s) such as oxygen, sulfur and nitrogen atom.

Preferable unsaturated heterocyclic group containing tertiary nitrogen atom, which may be substituted by suitable substituent(s) may be unsaturated 3 to 8-membered, more preferably 5 or 6-membered, heteromonocyclic group containing 1 to 4 nitrogen atom(s), for example, pyrrolyl (e.g. pyrrol-1-yl, etc.), pyrrolinyl (e.g. 2-pyrrolin-1-yl, etc.), imidazolyl, imidazolinyl (e.g. 2-imidazolinyl 4-imidazolin-1-yl, etc), pyrazolyl, pyrazolinyl (e.g. pyrazolin-1-yl, etc.), pyridyl, dihydropyridyl (e.g. 1,4-dihydropyridin-1-yl, etc.), tetrahydropyridyl [e.g. 1,2,3,6-tetrahydropyridin-1-yl, etc.], pyrimidinyl, pyrazinyl, pyridazinyl, triazinyl [e.g. 1,3,5-triazinyl, 1,2,4-triazinyl and 1,2,3-triazinyl], tetrahydrotriazinyl [e.g. 1,2,5,6-tetrahydro-1,2,4-triazin-1-yl, 1,4,5,6-tetrahydro-1,2,4-triazin-1-yl, etc.], triazolyl [e.g. 1H-1,2,4-triazolyl, 1H-1,2,3-triazolyl, 2H-1,2,3- triazolyl, etc.], tetrazinyl, tetrazolyl [e.g. 1H-tetrazolyl and 2H-tetrazolyl], etc.;

unsaturated 3 to 8-membered, more preferably 5 or 6-membered, heteromonocyclic group containing 1 to 2 oxygen atom(s) and 1 to 3 nitrogen atom(s), for example, oxazolyl, isoxazolyl, oxadiazolyl, (e.g. 1,2,4-oxadiazolyl, 1,3,4-oxadiazolyl, 1,2,5-oxadiazolyl, etc.), etc.;

unsaturated 3 to 8-membered, more preferably 5 or 6-membered, heteromonocyclic group containing 1 to 2 sulfur atom(s) and 1 to 3 nitrogen atom(s), for example, 1,3-thiazolyl, 1,2-thiazolyl, thiazolinyl, thiadiazolyl (e.g. 1,2,4-thiadiazolyl, 1,3,4-thiadiazolyl, 1,2,5-thiadiazolyl, 1,2,3-thiadiazolyl), etc.; and the like, wherein said heterocyclic group may be substituted by one or more, preferably one to three suitable substituent(s) such as those given for the explanation of "unsaturated heterocyclic group which may be substituted by suitable substituent(s)".

And further in case that said heterocyclic group is imidazolyl, pyrazolyl or imidazolinyl, the imino-moiety(ies) thereof may be protected by conventional imino-protective group(s) as mentioned below.

Preferable example of unsaturated heterocyclic group containing tertiary nitrogen atom, which may be substituted by suitable substituent(s) may be:

imidazolyl (e.g. imidazol-1-yl, etc);
pyrazolyl (e.g. pyrazol-1-yl, etc);
imidazolin-1-yl (e.g. 4-imidazolin-1-yl, etc);
2-oxoimidazolin-1-yl (e.g. 2-oxo-4-imidazolin-1-yl-, etc).

Suitable "unsaturated heterocyclic group containing quaternary nitrogen atom, which may be substituted by suitable substituent(s)" may be the same as those for "unsaturated heterocyclic group containing tertiary nitrogen atom", in which the tertiary nitrogen atom is substituted by "lower alkyl optionally substituted by a group consisting of carboxy and acyl" for "$R^6$" as mentioned below to form tertiary nitrogen atom. And further in case that said heterocyclic group is imidazolyl, pyrazolyl or imidazolinyl, the imino-moiety(ies) thereof may be protected by conventional imino-protective group(s) as mentioned below.

Preferable example of unsaturated heterocyclic group containing quaternary nitrogen atom, which may be substituted by suitable substituent(s) may be:

imidazolio.

Suitable "imino-protective group" may include acyl such as carbamoyl, aliphatic acyl, aromatic acyl, heterocyclic acyl and aliphatic acyl substituted with aromatic or heterocyclic group(s) derived from carboxylic, carbonic, sulfonic and carbamic acids.

The aliphatic acyl may include saturated or unsaturated, acyclic or cyclic ones, for example, alkanoyl such as lower alkanoyl (e.g. formyl, acetyl, propionyl, butyryl, isobutyryl, valeryl, isovaleryl, pivaloyl, hexanoyl, etc.), alkylsulfonyl such as lower alkylsulfonyl (e.g. mesyl, ethylsulfonyl, propylsulfonyl, isopropylsulfonyl, butylsulfonyl, isobutylsulfonyl, pentylsulfonyl, hexylsulfonyl, etc.), carbamoyl, N-alkylcarbamoyl (e.g. methylcarbamoyl, ethylcarbamoyl, etc.), alkoxycarbonyl such as lower alkoxycarbonyl (e.g. methoxycarbonyl, ethoxycarbonyl, propoxycarbonyl, butoxycarbonyl, t-butoxycarbonyl, etc.), alkenyloxycarbonyl such as lower alkenyloxycarbonyl (e.g. vinyloxycarbonyl, allyloxycarbonyl, etc.), alkenoyl such as lower alkenoyl (e.g. acryloyl, methacryloyl, crotonoyl, etc.), cycloalkanecarbonyl such as cyclo(lower)alkanecarbonyl (e.g. cyclopropanecarbonyl, cyclopentanecarbonyl, cyclohexanecarbonyl, etc.), and the like.

The aliphatic acyl substituted with aromatic group(s) may include aralkoxycarbonyl such as phenyl(lower)alkoxycarbonyl (e.g. benzyloxycarbonyl, phenethyloxycarbonyl, etc.), and the like.

These acyl groups may be further substituted with one or more suitable substituent(s) such as nitro, and the like, and preferable acyl having such substituent(s) may be nitroaralkoxycarbonyl(e.g. nitrobenzyloxycarbonyl, etc.), and the like.

More preferable example of "imino-protective group" thus defined may be $C_2$-$C_4$ alkenyloxycarbonyl and phenyl(or nitrophenyl)($C_1$-$C_4$)alkoxycarbonyl and the most preferable one may be 4-nitrobenzyloxycarbonyl.

Suitable "lower alkylene" may include straight or branched one such as methylene, ethylene, trimethylene, tetramethylene, pentamethylene, hexamethylene, methylmethylene, ethylethylene, propylene, and the like, in which more preferable example may be $C_1$-$C_4$ alkylene and the most preferable one may be methylene.

Suitable "acid residue" may include an inorganic acid residue such as azido, halogen (e.g. chlorine, bromine, fluorine or iodine), and the like, an organic acid residue such as acyloxy (e.g. benzenesulfonyloxy, tosyloxy, methanesulfonyloxy, etc.), and the like, in which more preferable example may be halogen and the most preferable one may be iodine.

Suitable "lower alkyl substituted by a group consisting of carboxy and acyl" may include aforementioned lower alkyl group, which is substituted by one or more, preferably one to three suitable substituent(s) such as carboxy, acyl as mentioned above, and the like, in which more preferable example may be carboxy($C_1$-$C_4$)alkyl, phenyl(or nitrophenyl)($C_1$-$C_4$)alkoxycarbonyl($C_1$-$C_4$)alkyl, ($C_1$-$C_4$)alkanoyl($C_1$-$C_4$)alkyl and carbamoyl($C_1$-$C_4$)alkyl and the most preferable one may be carboxymethyl, 4-nitrobenzyloxycarbonylmethyl, acetonyl and carbamoylmethyl.

Suitable "lower alkanimidoyl" may be straight or branched one such as formimidoyl, acetimidoyl, propionimidoyl, butyrimidoyl, isovalerimidoyl, pentanimidoyl, hexanimidoyl, and the like, in which more preferable one may be ($C_1$-$C_4$)alkanimidoyl and the most preferable one may be formimidoyl.

The processes for the preparation of the object compound (I) of the present invention are explained in detail in the following.

(1) Process 1

The compound (I) or salts thereof can be prepared by reacting the compound (II) or a reactive derivative at the oxo group thereof or salts thereof with the compound (III) or salts thereof.

Suitable salts of the compound (II) may be salts with bases such as those given for the compound (I).

The reactive derivative at the oxo group of the compound (II) can be represented by the following formula (II'), which is preferably used in this reaction and can be prepared by reacting the compound (II) or salts thereof with an acylating agent.

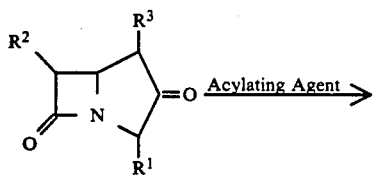

(II)
or salts thereof

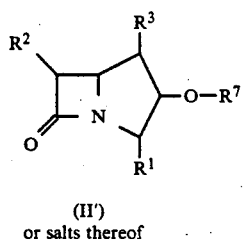

(II')
or salts thereof in which

R$^1$, R$^2$ and R$^3$ are each as defined above, and

R$^7$ is acyl as exemplified for the imino-protective group and further O,O-substituted phosphono derived from, for example, organic phosphoric acid mentioned hereinbelow.

Suitable acylating agents may include conventional ones which can introduce the acyl group as mentioned above into the compound (II), and preferable acylating agents may be organic sulfonic or phosphoric acid or its reactive derivative such as acid halide, acid anhydride, and the like, for example, arenesulfonyl halide (e.g. benzenesulfonyl chloride, p-toluenesulfonyl chloride, p-nitrobenzenesulfonyl chloride, p-bromobenzenesulfonyl chloride, etc.), arenesulfonic anhydride (e.g. benzenesulfonic anhydride, p-toluenesulfonic anhydride, p-nitrobenzenesulfonic anhydride, etc.), lower alkanesulfonyl halide which may have additional halogen (e.g. methanesulfonyl chloride, ethanesulfonyl chloride, trifluoromethanesulfonyl chloride, etc.), lower alkanesulfonic anhydride which may have halogen (e.g. methanesulfonic anhydride, ethanesulfonic anhydride, trifluoromethanesulfonic anhydride, etc.), di(lower)alkyl phosphorohaloridate (e.g. diethyl phosphorochloridate, etc.), diaryl phosphorohaloridate (e.g. diphenyl phosphorochloridate, etc.), and the like.

This acylation reaction is usually carried out in a conventional solvent which does not adversely influence the reaction such as acetone, dioxane, acetonitrile, chloroform, dichloromethane, hexamethylphosphoramide, dichloroethane, tetrahydrofuran, ethyl acetate, dimethylsulfoxide, N,N-dimethylformamide, pyridine, etc., or a mixture thereof.

When the acylating agent is used in a free acid form or its salt form in this reaction, the reaction is preferably carried out in the presence of a conventional condensing agent such as carbodiimide compound [e.g. N,N'-diethylcarbodiimide, N,N'-diisopropylcarbodiimide, N,N'-dicyclohexylcarbodiimide, N-cyclohexyl-N'-morpholinoethylcarbodiimide, N-cyclohexyl-N'-(4-diethylaminocyclohexyl)carbodiimide, N-ethyl-N'-(3-dimethylaminopropyl)carbodiimide, etc.]; N,N'-carbonyldiimidazole, N,N'-carbonylbis(2-methylimidazole); keteneimine compound (e.g. pentamethyleneketene-N-cyclohexylimine, diphenylketene-N-cyclohexylimine, etc.); ethoxyacetylene; 1-alkoxy-1-chloroethylene; ethyl polyphosphate; isopropylpolyphosphate; phosphorus oxychloride; phosphorus trichloride; thionyl chloride; oxalyl chloride; a combination of triphenylphosphine with carbon tetrachloride or diazenedicarboxylate; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; and the like.

This acylation reaction may be carried out in the presence of an inorganic or organic base such as an alkali metal bicarbonate (e.g. sodium bicarbonate, potassium bicarbonate, etc.), alkali metal carbonate (e.g. sodium carbonate, potassium carbonate, etc.), alkaline earth metal carbonate (e.g. magnesium carbonate, calcium carbonate, etc.), tri(lower)alkylamine (e.g. trimethylamine, triethylamine, N,N-diisopropyl-N-ethylamine, etc.), pyridine compound [e.g. pyridine, picoline, lutidine, N,N-di(lower)alkylaminopyridine such as N,N-dimethylaminopyridine, etc.], quinoline, N-lower alkylmorpholine (e.g. N-methylmorpholine, etc.), N,N-di(lower)alkylbenzylamine (e.g. N,N-dimethylbenzylamine, etc.), alkali metal alkoxide (e.g. sodium methoxide, sodium ethoxide, potassium butoxide, etc.), and the like.

The reaction temperature of this acylation reaction is not critical and the reaction is usually carried out under from cooling to warming.

With regard to the compound (II), it is to be noted that the 3,7-dioxo-1-azabicyclo[3.2.0]heptane ring system of the following formula (IIA) is well known to lie to tautomeric relation with the 3-hydroxy-7-oxo-1-azabicyclo[3.2.0]hept-2-ene ring system of the following formula (IIB), and accordingly, it is to be understood that both of these ring systems are substantially the same.

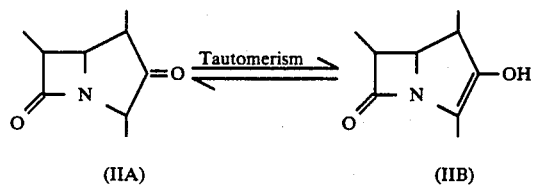

(IIA)                               (IIB)

The compound (II') or salts thereof can be used with or without isolation for the subsequent reaction with the compound (III) or salts thereof.

Suitable salts of the compound (III) may be the same as those for the compound (I) and silver salt.

The reaction of the compound (II) or its reactive derivative or salts thereof with the compound (III) or salts thereof can be carried out in the presence of an organic or inorganic base such as those given in the explanation of the acylation reaction as stated above.

This reaction can be carried out in a conventional solvent which does not adversely influence the reaction such as those given in the explanation of the acylation reaction.

The reaction temperature is not critical and the reaction is usually carried out under from cooling to warming.

(2) Process 2

The compound (I-b) or salts thereof can be prepared by subjecting the compound (I-a) or salts thereof to removal reaction of the carboxy-protective group on $R^1_a$.

Suitable salts of the compounds (I-a) and (I-b) may be the same as those for the compound (I).

The present reaction is usually carried out by a conventional method such as hydrolysis, reduction, and the like.

(i) Hydrolysis

Hydrolysis is preferably carried out in the presence of a base or an acid. Suitable base may include an alkali-metal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), and alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

In case that the hydroxy-protective group is tri(-lower)alkylsilyl, the hydrolysis can be carried out in the presence of tri(lower)alkylammonium halide (e.g. tributylammonium fluoride, etc.).

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base or acid can be also used as the solvent.

The reaction temperature is not critical and the reaction is usually carried out under from cooling to heating (ii) Reduction The reduction method applicable for this removal reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.), and the like.

In case that the catalytic reduction is applied, the reaction is preferably carried out around neutral condition.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

In case that the carboxy-protective group is allyl group, it can be deprotected by hydrogenolysis using a palladium compound.

Suitable palladium compound used in this reaction may be palladium on carbon, palladium hydroxide on carbon, palladium chloride, a palladium-ligand complex such as tetrakis(triphenylphosphine)palladium(0), bis(-dibenzylideneacetone)palladium(0), di[1,2-bis(diphenyl phosphino)ethane]palladium(0), tetrakis(triphenyl phosphite)palladium(0), tetrakis(triethyl phosphite)palladium(0), and the like.

The reaction can preferably be carried out in the presence of a scavenger of allyl group generated in situ, such as amine (e.g. morpholine, N-methylaniline, etc.), an activated methylene compound (e.g. dimedone, benzoylacetate, 2-methyl-3-oxovaleric acid, etc.), a cyanohydrin compound (e.g. α-tetrahydropyranyloxybenzyl cyanide, etc.), lower alkanoic acid or a salt thereof (e.g. formic acid, acetic acid, ammonium formate, sodium acetate, etc.), N-hydroxysuccinimide, and the like.

This reaction can be carried out in the presence of a base such as lower alkylamine (e.g. butylamine, triethyamine, etc.), pyridine, and the like.

When palladium-ligand complex is used in this reaction, the reaction can preferably be carried out in the presence of the corresponding ligand (e.g. triphenylphosphine, triphenyl phosphite, triethyl phosphite, etc.).

This reaction is usually carried out in a conventional solvent which does not adversely influence the reaction such as water, methanol, ethanol, propanol, dioxane, tetrahydrofuran, acetonitrile, chloroform, dichloromethane, dichloroethane, ethyl acetate, etc., or a mixture thereof.

The removal reaction can be selected according to the kind of carboxy-protective group to be removed.

The present process includes within the scope thereof a case that the hydroxy- and/or carboxy- and/or amino-protective group(s) on $R^2$ and/or $R^4$, and/or imino-protective group of $R^5$, and/or additional carboxy-protective group are removed at the same time during the reaction.

(3) Process 3

The compound (I-d) or salts thereof can be prepared by subjecting the compound (I-c) or salts thereof to removal reaction of the imino-protective group on $R^5_a$.

Suitable salts of the compounds (I-c) and (I-d) may be the same as those for the compound (I).

This reaction is usually carried out by a conventional method such as hydrolysis, reduction and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

The present process includes within the scope thereof a case that the carboxy- and/or hydroxy- and/or amino-protective group(s) on $R^1$ and/or $R^2$ and/or $R^4$, and/or additional carboxy-protective group are removed at the same time during the reaction.

(4) Process 4

The compound (I-f) or salts thereof can be prepared by subjecting the compound (I-e) or salts thereof to removal reaction of the hydroxy-protective group on $R^2_a$.

Suitable salts of the compounds (I-e) and (I-f) may be the same as those for the compound (I).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

In case that the hydroxy-protective group is tri(-lower)alkylsilyl, the removal of this protective group can also be carried out in the presence of tetra(lower)alkylammonium fluoride (e.g. tetrabutylammonium fluoride, etc.).

The present process includes within the scope thereof a case that the carboxy- and/or hydroxy- and/or amino-protective group(s) on $R^1$ and/or $R^4$, and/or the imino-protective group of R5, and/or additional carboxy-protective group are removed at the same time during the reaction.

(5) Process 5

The compound (I-h) or salts thereof can be prepared by reacting the compound (I-g) or salts thereof with the compound (IV).

Suitable salts of the compounds (I-g) and (I-h) may be the same as those for the compound (I).

This reaction is usually carried out in a conventional solvent which does not adversely influence the reaction such as water, dioxane, tetrahydrofuran, acetone, acetonitrile, etc., or a mixture thereof.

The reaction temperature is not critical, and the reaction is usually carried out under from cooling to warming.

(6) Process 6

The compound (I-i) or salts thereof can be prepared by reacting the compound (I-d) or salts thereof with lower alkanimidoylating agent.

Suitable salts of the compound (I-i) may be the same as those for the compound (I).

Suitable lower alkanimidoylating agent may be conventional ones which can introduce the lower alkanimidoyl group as mentioned above into the compound (I-d), and said preferable agent may be lower alkyl(-lower)alkanimidate (e.g. methyl formimidate, ethyl formimidate, methyl acetimidate, ethyl acetimidate, ethyl propionimidate, ethyl butyrimidate, ethyl isovalerimidate, ethyl pentanimidate, ethyl hexanimidate, etc.), ar(lower)alkyl lower alkanimidate (e.g. benzyl formimidate, etc.), (lower)alkanimidoyl halide (e.g. formimidoyl chloride, formimidoyl bromide, acetimidoyl chloride, acetimidoyl, bromide, propionimidoyl chloride, butyrimidoyl chloride, isovalerimidoyl chloride, pentanimidoyl chloride, hexanimidoyl chloride, etc.), and the like, or an acid addition salt thereof.

This reaction is usually carried out in a conventional solvent which does not adversely influence the reaction such as tetrahydrofuran, dioxane, water, methanol, ethanol, buffer solution (e.g. phosphate buffer, etc.), etc., or a mixture thereof.

The reaction temperature is not critical, and the reaction is usually carried out under from cooling to warming.

Methods A and B for preparing the new starting compound (III) or salts thereof are explained in detail in the following.

(A) Method A

The compound (III-a) or salts thereof can be prepared by reacting the compound (IV) or a reactive derivative at the hydroxy group thereof or salts thereof with the compound (V) or salts thereof.

Suitable salts of the compounds (III-a), (IV) may be the same as those for the compound (I).

Suitable salts of the compound (V) may be salts with bases such as those given for the compound (I).

Suitable reactive derivative at the hydroxy group of the compound (IV) may include a conventional one such as halide (e.g. chloride, bromide, iodide, etc.), sulfonate (e.g. methanesulfonate, benzenesulfonate, toluenesulfonate, etc.), and the like, in which more preferable example may be sulfonate.

The starting compound (IV) of this method is new and can be prepared by the methods described in the Preparations mentioned below.

Preferable example of the compound (V) may be ar(lower)alkanethiol such as mono- or di- or triphenyl(-lower)alkanethiol (e.g. phenylmethanethiol, diphenylmethanethiol, triphenylmethanethiol, etc.), thio(lower-)alkanoic S-acid (e.g. thioacetic S-acid, etc.) or salts thereof, thioarenoic S-acid or salts thereof (e.g. thiobenzoic S-acid, etc.), and the like, in which more preferable example may be triphenyl($C_1$–$C_4$)alkanethiol, thio($C_1$–$C_4$)alkanoic S-acid or alkali metal salts thereof and thio($C_6$–$C_{10}$)arenoic S-acid or alkali metal salts thereof, and the most preferable one may be triphenylmethanethiol, thioacetic S-acid and potassium thioacetate.

In case that the compound (V) may be ar(lower)alkanethiol, the starting compound (IV) of the present reaction is preferably used in the form of its reactive derivative at the hydroxy group, and in such a case, this reaction is usually carried out in the presence of an organic or inorganic base such as those exemplified in the explanation of Process 2.

In case that suitable example of compound (V) may be thio(lower)alkanoic S-acid or thioarenoic S-acid, this exaction is preferably carried out in the presence of a conventional condensing agent such as combination of triarylphosphine (e.g. triphenylphosphine, etc.) and di(lower)alkyl azodicarboxylate (e.g. diethyl azodicarboxylate, etc.).

This reaction is usually carried out in a conventional solvent which does not adversely influence the reaction such as dichloromethane, methanol, ethanol, propanol, pyridine, N,N-dimethylformamide, 4-methyl-2-pentanone, tetrahydrofuran, etc., or a mixture thereof.

The reaction temperature is not critical and the reaction is usually carried out under from cooling to warming.

In this method, the configuration on the carbon atom substituted with the hydroxy group of the compound (IV) is inverted in the compound (III-a).

(B) Method B

The compound (III) or salts thereof can be prepared by subjecting the compound (III-a) or salts thereof to elimination reaction of the mercapto-protective group.

This elimination reaction can be carried out by a conventional method as described below, which can be selected according to the kind of mercapto-protective group to be eliminated.

In case that the protective groups may be ar(lower)alkyl group, it can generally be eliminated by treating, for example, with a silver compound (e.g. silver nitrate, silver carbonate, etc.).

The reaction with the silver compound as stated above is preferably carried out in the presence of an organic base (e.g. pyridine, etc.).

The resultant silver salt of compound (III) can be transformed into its alkali metal salt, if necessary, by reacting with alkali metal halide (e.g. sodium iodide, potassium iodide, etc.).

Further, in case that the protective groups may be acyl group, it can generally be eliminated by solvolysis such as hydrolysis using an acid or base, alcoholysis using a base, and the like.

Suitable acid or base used in these reactions may be the same such as those given in the explanation of hydrolysis of the Process 2.

The hydrolysis is usually carried out in a conventional solvent which does not adversely influence the reaction such as water, alcohol (e.g. methanol, ethanol, etc.), pyridine, N,N-dimethylformamide, etc., or a mixture thereof, and further in case that the base or acid to be used is in liquid, it can also be used as a solvent.

The alcoholysis is usually carried out in a conventional alcohol such as methanol, ethanol, and the like.

The reaction temperature is not critical and the reaction is usually carried out under from cooling to warming.

The object compounds (I), (I-b), (I-d), (I-f), (I-h) and (I-i) obtained according to the Processes 1 to 6, can be isolated and purified in a conventional manner, for example, extraction, precipitation, fractional crystallization, recrystallization, chromatography, and the like.

The object compound (I) and pharmaceutically acceptable salts thereof of the present invention are novel and exhibit high antimicrobial activity, inhibiting the growth of a wide variety of pathogenic microorganisms including Gram-positive and Gram-negative microorganisms and are useful as antimicrobial agents.

In the present invention, the object compound (I) possessing more potent antimicrobial activity can be represented by the following formula:

<chemical structure>
R²ᵦ, R³, A—R⁴, S, N, O, COOH, NH
</chemical structure> in which $R^2_b$, $R^3$, $R^4$ and A are each as defined above, and pharmaceutically acceptable salts thereof.

Particularly, the compound (I) possessing the most potent antimicrobial activity can be represented by the following formula:

<chemical structure>
HO, H, H, R³, A—R⁴, S, N, O, COOH, NH
</chemical structure> in which $R^3$, $R^4$ and A are each as defined above, and pharmaceutically acceptable salts thereof.

Now in order to show the utility of the object compound (I), the test data on antimicrobial activity of the representative compound of the compound (I) of this invention is shown in the following.

in vitro Antimicrobial Activity

Test Method in vitro Antimicrobial Activity was determined by the two-fold agar-plate dilution method as described blow.

One loopful of an overnight culture of a test strain in Trypticase-soy broth ($10^6$ viable cells per ml) was streaked on heart infusion agar (HI-agar) containing graded concentrations of the test compound, and the minimal inhibitory concentration (MIC) was expressed in terms of μg/ml after incubation at 37° C. for 20 hours.

Test Compound

The compound of Example 2.

Test Result

| Test Strain | MIC (μg/ml) |
| --- | --- |
| E. Coli 31 | 0.05 |

For therapeutic administration, the object compound (I) and the pharmaceutically acceptable salts thereof of the present invention are used in the form of conventional pharmaceutical preparation which contains said compound, as an active ingredient, in admixture with pharmaceuticallyly acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade, and the like.

If needed, there may be included in the above preparations auxiliary substances, stabilizing agents, wetting agents and other commonly used additives such as lactose, stearic acid, magnesium stearate, terra alba, sucrose, corn starch, talc, gelatin, agar, pectin, peanut oil, olive oil, cacao butter, ethylene glycol, tartaric acid, citric acid, fumaric acid, and the like.

While the dosage of the compound (I) may vary from and also depend upon the age, conditions of the patient, a kind of diseases, a kind of the compound (I) to be applied, etc. In general, amount between 1 mg and about 4,000 mg or even more per day may be administered to a patient. An average single dose of about 1 mg, 10 mg, 50 mg, 100 mg, 250 mg, 500 mg, 1000 mg, 2000 mg, of the object compound (I) of the present invention may be used in treating diseases infected by pathogenic microorganisms.

The following Preparations and Examples are given for the purpose of illustrating this invention in more detail.

Preparation 1-1

A solution of methanesulfonyl chloride (4.53 ml) in dichloromethane (20 ml) was dropwise added to a solution of (2S,4R)-4-t-butyldimethylsilyloxy-2-hydroxymethyl-1-(4-nitrobenzyloxycarbonyl)pyrrolidine (20.0 g) in a mixture of triethylamine (8.85 ml) and dichloromethane (200 ml) with stirring under ice-cooling. The mixture was stirred under the same condition for 30 minutes, washed with water, saturated aqueous sodium hydrogen carbonate and brine, in turn, dried over magnesium sulfate, and concentrated under reduced pressure to give (2S,4R)-4-t-butyldimethylsilyloxy-2-methanesulfonyloxy-methyl-1-(4-nitrobenzyloxycarbonyl)pyrrolidine.

Preparation 1-2

(2S,4R)-1-Benzyloxycarbonyl-4-t-butyldimethylsilyloxy-2-methanesulfonyloxymethylpyrrolidine was obtained in 88% yield in substantially the same manner as that of Preparation 1-1).
IR (Neat) : 1710–1690 cm$^{-1}$
NMR (CDCl$_3$,δ) 0.50 (6H, s), 0.87 (9H, s), 1.8–2.15 (2H, m), 2.90 (3H, s), 3.4–3.5 (2H, m), 4.1–4.65 (4H, m), 5.14 (2H, s), 7.33 (5H, s)

Preparation 2-1)

A mixture of (2S,4R)-4-t-butyldimethylsilyloxy-2-methanesulfonyloxymethyl-1-(4-nitrobenzyloxycarbonyl) pyrrolidine obtained in Preparation 1-1) and sodium iodide (10.95 g) in dimethylformamide (100 ml) was heated at 70–75° C. for 8 hours with stirring. The mixture was poured into ice-water (500 ml) and extracted with ethyl acetate (300 ml ×3). The organic layers were combined, dried over magnesium sulfate and concentrated under reduced pressure to give a syrup. The syrup was subjected to a column chromatography on silica gel (200 g) and eluted with chloroform to give (2S,4R)-4-t-butyldimethylsilyloxy2-iodomethyl-1-(4-nitrobenzyloxycarbonyl) pyrrolidine (15.0g).
mp : 105–106° C.
IR (Nujol) : 1690 cm$^{-1}$
NMR (CDCl$_3$, δ) : 0.07 (6H, s), 1.85 (9H, s), 1.7–2.3 (2H, m), 3.4–4.1 (5H, m), 4.40 (1H, m), 5.27 (2H, s), 7.52 (2H, d, J=8.5Hz), 8.21 (2H, d, J=8.5Hz)

Preparation 2-2)

(2S,4R)-1-Benzyloxycarbonyl-4-t-butyldimethylsilyloxy-2-iodomethylpyrrolidine was obtained in 66% yield in substantially the same manner as that of Preparation 2-1).
IR (Neat) : 1710–1695 cm$^{-1}$
NMR (CDCl$_3$, δ) : 0.50 (6H, s), 0.87 (9H, s), 1.75–2.2 (2H, m), 3.3–4.1 (5H, m), 4.25–4.45 (1H, m), 5.13 (2H, s), 7.30 (5H, s)

Preparation 3-1)

A mixture of (2S,4R)-4-t-butyldimethylsilyloxy-2-iodomethyl-1-(4-nitrobenzyloxycarbonyl)pyrrolidine (3.00 g) and imidazole (15.0 g) was fused at 100–110° C. for 5 hours with stirring. The mixture was poured into ice-water (150 ml) and extracted with chloroform (50 ml ×3). The organic layers were combined, washed with water, dried over magnesium sulfate and concentrated under reduced pressure to give a syrup. The syrup was subjected to a column chromatography on silica gel (30 g) and eluted with a mixture of methanol and chloroform (1:99, V/V) to give (2S,4R)-4-t-butyldimethylsilyloxy-2-(imidazol-1-yl)-methyl-1-(4-nitrobenzyloxycarbonyl) pyrrolidine (1.57 g).
IR (Neat) : 1705 cm$^{-1}$
NMR (CDCl$_3$, δ) : 0.01 (6H, s), 0.82 (9H, s), 5.25 (2H, d, J=3Hz), 6.78 (1H, s), 7.01 (1H, s), 7 33 (1H, s), 7.48 (2H, d, J=8Hz), 8.19 (2H, d, J=8.5Hz)

Preparation 3-2)

(2S,4R)-1-Benzyloxycarbonyl-4-t-butyldimethylsilyloxy-2-(imidazol-1-yl)methylpyrrolidine was obtained in 53% yield in substantially the same manner as that of Preparation 3-1).
IR (Neat) : 1705–1695 cm$^{-1}$ Preparation 4-1)

Conc. hydrochloric acid (0.5 ml) was added to a solution of (2S,4R)-4-t-butyldimethylsilyloxy-2-(imidazol-1-yl)methyl-1-(4-nitrobenzyloxycarbonyl) pyrrolidine (1.55 g) in methanol (15 ml). After stirring at ambient temperature for one hour, saturated aqueous sodium hydrogen carbonate (3 ml) was added to the mixture. The reaction mixture was concentrated under reduced pressure to give a residue. To the residue was added a mixture of chloroform (30 ml) and water (30 ml). The organic layer was separated, dried over magnesium sulfate and concentrated under reduced pressure to give a syrup. The syrup was subjected to a column chromatography on silica gel (20 g) and eluted with a mixture of methanol and chloroform (2:98, V/V) to give (2S,4R)-4-hydroxy-2-(imidazol-1-yl)methyl-1-(4-nitrobenzyloxycarbonyl)-pyrrolidine (0.80 g).
mp : 147–148° C.
IR (CHCl$_3$, δ) : 1710–1690 cm$^{-1}$
NMR (CDCl$_3$, δ) : 1.5–2.2 (2H, m), 3.1–3.7 (3H, m), 3.9–4.5 (4H, m), 5.26 (2H, s), 6.78 (1H, s), 6.96 (1H, s), 7.33 (1H, s), 7.50 (2H, d, J=8Hz), 8.20 (2H, d, J=8Hz)

Preparation 4-2)

(2S,4R)-1-Benzyloxycarbonyl-4-hydroxy-2-(imidazol-1-yl(methylpyrrolidine was obtained in 96% yield in substantially the same manner as that of Preparation 4-1).
mp : 107–108° C.
IR (KBr) : 1695 cm$^{-1}$
NMR (CDCl$_3$, δ) : 1.5–2.1 (2H, m), 3.0–4.7 (7H, m), 5.13 (2H, s), 6.70 (1H, s), 6.88 (1H, s), 7.23 (1H, s), 7.30 (5H, s)

Preparation 5-1)

Methanesulfonyl chloride (0.40 ml) was added to a suspension of (2S,4R)-4-hydroxy-2-(imidazol-1-yl)methyl-1-(4-nitrobenzyloxycarbonyl)pyrrolidine (0.79g) in a mixture of triethylamine (0.80 ml), tetrahydrofuran (16 ml) and dichloromethane (24 ml) at 0–5° C., and the mixture was stirred at 0–5° C. for one hour. The reaction mixture was poured into a mixture of water (50 ml) and dichloromethane (20 ml). The organic layer was separated, dried over magnesium sulfate and concentrated under reduced pressure to give a syrup. The syrup was subjected to a column chromatography on silica gel (20 g) and eluted with a mixture of methanol and chloroform (2:98, V/V) to give (2S,4R)-2-(imidazol-1-yl)methyl-4-methanesulfonyloxyl-(4-nitrobenzyloxycarbonyl)pyrrolidine (0.78 g).
IR (CHCl$_3$) : 1705 cm$^{-1}$ NMR (CDCl₃, δ) : 3.00 (3H, s), 5.27 (2H, s), 6.80 (1H, s), 7.03 (1H, s), 7.40 (1H, s), 7.50 (2H, d, J=8Hz), 8.22 (2H, d, J=8Hz)

Preparation 5-2)

(2S,4R)-1-Benzyloxycarbonyl-2-(imidazol-1-yl)mEthyl-4-methanesulfonyloxypyrrolidine was obtained quantitatively in substantially the same manner as that of Preparation 5-1).

IR (Neat) : 1720 (sh), 1710–1685, 1500 cm⁻¹

NMR (CDCl₃, δ) : 1.72–1.92 (1H, m), 2.16–2.56 (1H, m), 2.90 (3H, s), 3.11–3.41 (1H, m), 3.69–4.51 (4H, m), 4.70–4.94 (1H, m), 5.17 (2H, s), 6.76 (1H, s), 6.98(1H, s), 7.34 (6H, s)

Preparation 6

(2S,4R)-4-Hydroxy-1-(4-nitrobenzyloxycarbonyl)-2-(pyrazol-1-yl)methylpyrrolidine was obtained in 75.3% yield in substantially the same manner as that of Preparation 3-1).

IR (Neat) : 1710–1675 cm⁻¹

Preparation 7

(2S,4R)-4-Methanesulfonyloxy-1-(4-nitrobenzyloxycarbonyl)-2-(pyrazol-1-yl)methylpyrrolidine was obtained in 59.5% yield in substantially the same manner as that of Preparation 5-1).

IR (Neat) : 1705 cm⁻¹

NMR (CDCl₃, δ) : 2.98 (3H, s), 5.31 (2H, s), 6.27 (1H, t, J=2.5Hz), 7.30 (1H, d, J=2.5Hz), 7.5–7.65 (3H, m), 8.27 (2H, d, J=8Hz)

Preparation 8

To a solution of (2S,4R)-2-aminomethyl-4-t-butyldimethylsilyloxy-1-(4-nitrobenzyloxycarbonyl)pyrrolidine (30.0 g) in water (150 ml) and tetrahydrofuran (450 ml) was added chloroacetyl chloride (6.4 ml) below 10° C., keeping the pH between 8-9 with 4N aqueous sodium hydroxide. The reaction mixture was poured into saturated aqueous sodium chloride (150 ml), the organic layer was separated, and the aqueous solution was extracted twice with ethyl acetate (100 ml). The organic layer was combined and washed with saturated aqueous sodium chloride, dried over magnesium sulfate and evaporated in vacuo to give crude (2S,4R)-4-t-butyldimethylsilyloxy-2-(chloroacetamido)methyl-1-(4-nitrobenzyloxycarbonyl)-pyrrolidine.

Precaration 9

A solution of crude (2S,4R)-4-t-butyldi-methylsilyloxy-2-(chloroacetamido)methyl-1-(4-nitrobenzyloxy carbonyl)pyrrolidine obtained in Preparation 8, potassium cyanate (59.3 g) and tetrabutylammonium iodide (27.0 g) in acetonitrile (600 ml) was refluxed for 1.5 hours. The reaction mixture was evaporated in vacuo, and the resulting residue was poured into saturated aqueous sodium chloride, and then extracted twice with ethyl acetate. The organic layer was washed with saturated aqueous sodium chloride, dried over magnesium sulfate and evaporated in vacuo to give crude (2S,4R]-4-t-butyldimethylsilyloxy-2-(2,4-dioxoimidazolidin-3-yl)methyl-1-(4-nitrobenzyloxycarbonyl)pyrrolidine.

Preparation 10

A solution of crude (2S,4R)-4-t-butyldimethylsilyloxy-2-(2,4-dioxoimidazolidin-3-yl)methyl-1-(4-nitrobenzyloxycarbonyl)pyrrolidine obtained in Preparation 9 and conc. hydrochloric acid (12 ml) in methanol (500 ml) was stirred at room temperature for 1 hour and to the solution was added triethylamine (20 ml). The reaction mixture was evaporated in vacuo and the deposited crystal was removed by filtration, and then the filtrate was evaporated in vacuo. The resulting residue was chromatographed on silica gel (1 λ) eluting with a mixture of methanol and dichloromethane (1:9, V/V) to give crude (2S,4R)-2-(2,4-dioxoimidazolidin-3-yl-)methyl-4-hyiroxy-1-(4-nitrobenzyloxycarbonyl) pyrrolidine.

Preparation 11

To a suspension of sodium borohydr-ide (6.03 g) in tetrahydrofuran (270 ml) was added boron trifluoride etherate (72 ml) at 0° C. under stirring. After stirring for 10 minutes, to the suspension was added a solution of (2S,4R)-2-(2,4-dioxoimidazolidin-3-yl)methyl-4-hydroxy-1-(4-nitrobenzyloxycarbonyl)pyrrolidine (27.3 g) obtained in Preparation 10 in tetrahydrofuran (140 ml) and the mixture was stirred for 14 hours at ambient temperature. This reaction mixture was evaporated in vacuo and to the residue was added a solution of conc. hydrochloric acid (31 ml) in methanol (400 ml). After standing for 12 hours at ambient temperature, the solution was evaporated in vacuo and the resulting residue was poured into saturated aqueous sodium hydrogen carbonate (450 ml). The aqueous layer was extracted three times with a mixture of ethyl acetate (200 ml) and tetrahydrofuran (200 ml) and evaporated in vacuo. The resulting residue was chromatographed on silica gel (600 ml) eluting with a mixture of methanol and dichloromethane (5:95, V/V) to give (2S,4R)-4-hydroxy-1-(4-nitrobenzyloxycarbonyl)-2-(2-oxo-4-imidazolin-1-yl)methyl pyrrolidine (1.11 g).

IR (CH₂Cl₂): 1700, 1680, 1520, 1340 cm⁻¹

NMR (CDCl₃, δ) : 1.93–2.18 (2H, m), 2.98–4.47 (7H, m), 5.23 (2H, s), 6.04 (1H, m), 6.19 (1H, m), 7.48 (2H, d, J=9Hz), 8.14 (2H, d, J=9Hz), 9.66–10.17 (1H, br s)

Preparation 12

(2S,4R)-4-methanesulfonyloxy-1-(4-nitrobenzoxycarbonyl)-2-(2-oxo-4-imidazolin-1-yl) methylpyrrolidine (8.42 g) was obtained in 83.4% yield in substantially the same manner as that of Preparation 5-1).

IR (CH₂Cl₂): 1700, 1680, 1520, 1340 cm⁻¹

NMR (CDCl₃, δ) : 2.13–2.50 (2H, m), 3.03 (3H, s), 3.32–4.49 (6H, m), 5.20 (2H, s), 5.94–6.10 (1H, m), 6.14–6.31 (1H, m), 7.51 (2H, d, J=9Hz), 8.16 (2H, d, J=9Hz), 10.23–10.56 (1H, br s)

Preparation 13

To a solution of (2S,4R)-1-benzyloxycarbonyl-2-hydroxymethyl-4-methanesulfonyloxypyrrolidine (48.0 g) in dichloromethane (250 ml) was added triethylamine (26.4 ml) and methanesulfonyl chloride (14.3 ml) under ice-cooling and the mixture was stirred at the same temperature for 30 minutes. The reaction mixture was washed in turn with water (100 ml) and saturated aqueous sodium chloride (100 ml), dried over anhydrous magnesium sulfate and evaporated in vacuo to give (2S,4R)-1-benzyloxycarbonyl-4-methanesulfonyloxy-2-methanesulfonyloxymethylpyrrolidine (48.1 g).

NMR (CDCl₃, δ) : 2.04–2.60 (2H, m), 2.88 (3H, broad s), 3.01 (3H, s), 3.40–3.70 (1H, m), 3.90–4.10 (1H, m), 4.20–4.40 (2H, m), 5.10–5.30 (3H, m), 7.36 (5H, s)

Preparation 14

(2S,4R)-1-Benzyloxycarbonyl-4-methanesulfonyloxy-2-(imidazol-1-yl)methylpyrrolidine was obtained in 69.4% yield in substantially the same manner as that of Preparation 18.

NMR (CDCl$_3$, δ) : 1.72–1.92 (1H, m), 2.16–2.56 (1H, m), 2.90 (3H, s), 3.11–3.41 (1H, m), 3.69–4.51 (4H, m), 4.70–4.94 (1H, m), 5.17 (2H, s), 6.76 (1H, s), 6.98 (1H, s), 7.34 (6H, s)

Preparation 15

A mixture of (2S,4R)-1-benzyloxycarbonyl-2-(imidazol-1-yl)methyl-4-methanesulfonyloxypyrrolidine (8.60 g), conc. hydrochloric acid (1.76 ml), methanol (80 ml) and 10% palladium on carbon (50% wet) (4.50 g) was stirred for 6 hours under atmospheric pressure of hydrogen residue. The residue was dissolved in a mixture of tetrahydrofuran (22 ml) and water (22 ml). To the solution was added dropwise allyl chloroformate (2.5 ml) under ice-cooling, keeping pH 9–10 with 4N sodium hydroxide and then the mixture was stirred at the same condition for 30 minutes. To the reaction mixture were added sodium chloride (1.0 g) and ethyl acetate (10 ml). The organic layer was separated, washed with saturated aqueous sodium chloride, dried over anhydrous magnesium sulfate and evaporated in vacuo to give (2S,4R)-1-allyloxycarbonyl-2-(imidazol-1-yl)methyl-4-methanesulfonyloxypyrrolidine (5.85 g).

IR (Neat) : 1710–1685, 1650, 1510, 1410 cm$^{-1}$

NMR (CDCl$_3$, δ) : 1.83–1.97 (1H, m), 2.13–2.58 (1H, m), 3.01 (3H, s), 3.28 (1H, dd, J=4Hz, J=13Hz), 79–4.72 (6H, m), 4.80–4.92 (1H, m), 5.24–5.50 (2H, m), 5.87–6.07 (1H, m), 6.86 (1H, s), 7.07 (1H, s), 7.41 (1H, s)

Preparation 16

To a solution of (2S,4R)-1-allyloxycarbonyl-4-hydoxy2-methoxycarbonylpyrrolidine (10 g) in tetrahydrofuran (20 ml) and ethanol (30 ml) was added by portions sodium borohydride (3.30 g) with stirring at 25–30° C., and the mixture was stirred at the same temperature for 4 hours. To the reaction mixture was added dropwise conc. hydrochloric acid (7.27 ml) with stirring at 0–2° C. The resulting precipitates were filtered off and the filtrate was evaporated in vacuo. The resulting residue was dissolved in a mixture of tetrahydrofuran (20 ml), ethanol (20 ml) and saturated aqueous sodium chloride (50 ml). The organic layer was evaporated in vacuo to give (2S,4R)-1-allyloxycarbonyl-4-hydroxy-2-hydroxymethylpyrrolidine (9.48 g).

NMR (CDCl$_3$, δ) : 1.70–1.82 (1H, m), 1.90–2.05 (1H, 
NMR (CDCl$_3$, δ) : 1.70–1.82 (1H, m), 1.90–2.05 (1H, m), 2.51 (1H, broad s), 3.40–3.95 (5H, m), 4.40 (1H, broad s), 4.58–4.85 (3H, m), 5.10–5.38 (2H, m), 5.84–6.04 (1H, m)

Preparation 17

To a solution of (2S,4R)-1-allyloxycarbonyl-4-hydroxy-2-hydroxymethylpyrrolidine (9.48 g) in ethyl acetate (50 ml) were added successively triethylamine (15.74 ml) and methanesulfonyl chloride (8.02 ml) with stirring under ice-cooling, and the mixture was stirred at the same temperature for 30 minutes. Water (50 ml) was added to the reaction mixture. The organic layer was separated and washed twice with saturated aqueous sodium chloride (50 ml), dried over anhydrous magnesium sulfate and evaporated in vacuo. The resulting residue was chromatographed on silica gel (125 g) eluting successively with dichloromethane (500 ml) and a mixture of dichloromethane and methanol (19:1, V/V, 2.5g). The fractions containing the desired compound were collected and evaporated in vacuo to give (2S,4R)-1-allyloxycarbonyl-4-methanesulfonyloxy-2-(methanesulfonyloxy)methyl pyrrolidine (8.73 g).

IR (Neat) 1745 (sh), 1705 (sh), 1690, 1670, 1410 cm$^{-1}$

NMR (CDCl$_3$, δ) : 2.25–2.53 (2H, m), 3.00 (3H, s), 3.05 (3H, s), 3.50–3.70 (1H, m), 3.88–4.15 (1H, m), 4.25–4.35 (2H, m), 4.55–4.75 (3H, m), 5.17–5.31 (3H, m), 5.84–6.00 (1H, m)

Preparation 18

A mixture of (2S,4R)-1-allyloxycarbonyl-4-methanesulfonyloxy-2-(methanesulfonyloxy)methylpyrrolidine (8.73 g) and imidazole (4.16 g) was stirred at 70–75° C. for 7 hours. After cooling, the reaction mixture was dissolved in ethyl acetate (30 ml), water (30 ml) and conc. hydrochloric acid (8.0 ml) with stirring. The aqueous layer was separated, adjusted to pH 9.0 with 10% aqueous sodium hydroxide and extracted twice with ethyl acetate (50 ml). The extract was dried over anhydrous magnesium sulfate and evaporated in vacuo to give (2S,4R)-1-allyloxycarbonyl-2-(imidazol-1-yl)methyl-4-methanesulfonyloxypyrrolidine (5.30 g).

NMR (CDCl$_3$, δ) : 1.83–2.04 (1H, m), 2.20–2.55 (1H, m), 3.01 (3H, s), 3.23–3.35 (1H, m), 3.79–4.70 (6H, m), 4.80–4.90 (1H, m), 5.20–5.40 (2H, m) 5.87–6 07 (1H, m), 6.86 (1H, broad s), 7.07 (1H, broad s), 7.41 (1H, broad s)

Preparation 19-1)

A solution of (2S,4R)-2-(imidazol-1-yl)methyl-4-methanesulfonyloxy-1-(4-nitrobenzyloxycarbonyl) pyrrolidine (0.76 g) in dimethylformamide (2 ml) was added to a mixture of thioacetic S-acid (0.16 ml) and sodium hydride (62.8 % in oil suspension, 0.08 g) in dimethylformamide (5 ml) under nitrogen stream and the mixture was heated at 70–75° C. for 5 hours. The mixture was poured into ice-water (70 ml), extracted with ethyl acetate (70 ml), dried over magnesium sulfate and concentrated under reduced pressure to give a syrup. The syrup was subjected to a column chromatography on silica gel (20 g) and eluted with a mixture of methanol and chloroform (2:98, V/V) to give (2S,4S)-4-acetylthio-2-(imidazol-1-y-1)methyl-1-(4-nitrobenzyloxycarbonyl)pyrrolidine (0.38 g).

IR (Neat) : 1710–1690 cm$^{-1}$

NMR (CDCl$_3$, δ) : 2.33 (3H, s), 5.22 (2H, s), 6.80 (1H, s), 7.01 (1H, s), 7.37 (1H, s), 7.48 (2H, d, J=8Hz), 8.19 (2H, d, J=8Hz)

Preparation 19-2)

To a solution of calcium hydroxide (2.25 g) and (2S,4R)-1-allyloxycarbonyl-2-(imidazol-1-yl)methyl-4-methanesulfonyloxypyrrolidine (10 g) in 4-methyl-2-pentanone (60 ml) was added dropwise thioacetic S-acid (4.38 ml) with stirring below 45° C. The solvent (18 ml) of the mixture was removed under reduced pressure at 40–45° C. The resulting suspension was heated at 80–85° C. for 2 hours. After cooling, water (20 ml) and ethyl acetate (20 ml) was added to the reaction mixture. The insoluble material was filtered off and washed with ethyl acetate (30 ml). The filtrate and washing were combined. The organic layer was washed with saturated aqueous sodium chloride, dried over magnesium sulfate and evaporated in vacuo to give (2S,4S)-4-acetylthio-1-allyloxycarbonyl-2-(imidazol-1-yl)methylpyrrolidine (7.94 g).

NMR (CDCl₃, δ) : 1.60–1.72 (1H, m), 2.33 (3H, s), 2.35–2.48 (1H, m), 3.03–3.18 (1H, m), 3.79–4.29 (5H, m), 4.61–4.66 (2H, m), 5.12–5.39 (2H, m), 5.86–6.05 (1H, m), 6.89 (1H, s), 7.07 (1H, s), 7.51 (1H, s)

Preparation 19-3)

(2S,4S)-4-Acetylthio-1-(4-nitrobenzyloxycarbonyl)-2-(pyrazol-1-yl)methylpyrrolidine was obtained in 72.7% yield in substantially the same manner as that of Preparation 19-1).

IR (Neat) : 1710–1690 cm⁻¹

NMR (CDCl₃, δ) : 2.33 (3H, s), 5.28 (2H, s), 6.28 (1H, t, J=2.5Hz), 7.91 (1H, d, J=2.5Hz), 7.5–7.65 (3H, m), 8.30 (2H, d, J=8Hz)

Preparation 19-4)

(2S,4S)-4-Acetylthio-1-(4-nitrobenzyloxycarbonyl)-2(2-oxo-4-imidazolin-1-yl) methylpyrrolidine was obtained in 90.6% yield in substantially the same manner as that of Preparation 19-1).

IR (CH₂Cl₂) 1700, 1690, 1520, 1340 cm⁻¹

NMR (CDCl₃, δ) : 1.64–2.15 (2H, m), 2.33 (3H, s), 2.90–4.50 (6H, m), 5.22 (2H, s), 5.93–6.12 (1H, m), 6.12–6.29 (1H, m), 7.49 (2H, d, J=9Hz), 8.14 (2H, d, J=9Hz), 10.10–10.57 (1H, br s)

Preparation 20-1)

To a solution of (2S,4S)-4-acetylthio-2-(imidazol-1-yl)methyl-1-[4-nitrobenzyloxycarbonyl) pyrrolidine (0.37 g) in methanol (7 ml) was added a 28% solution (0.4 ml) of sodium methoxide in methanol at −10 to −5° C. under nitrogen stream, followed by stirring at the same temperature for 30 minutes. To the mixture was added acetic acid (0.15 ml) at the same temperature. The reaction mixture was concentrated under reduced pressure to give a residue. The residue was dissolved in ethyl acetate (50 ml), washed with water (50 ml), dried over magnesium sulfate and concentrated under reduced pressure to give a syrup. The syrup was subjected to a column chromatography on silica gel (10 g) and eluted with a mixture of methanol and chloroform (1:99 V/V) to give (2S,4S)-2-(imidazol-1-yl)-methyl-4-mercapto-1-(4-nitrobenzyloxycarbonyl)pyrrolidine (0.27 g).

IR (Neat) : 1710–1690 cm⁻¹

NMR (CDCl₃, δ) : 2.08 (3H, s), 5.22 (2H, s), 6.83 (1H, s), 7.05 (1H, s), 7.43 (1H, s), 7.51 (2H, d, J=8.5Hz), 8.22 (2H, d, J=8.5Hz)

Preparation 20-2)

(2S,4S)-1-Allyloxycarbonyl-2-(imidazol-1-yl)methyl-4mercaptopyrrolidine was obtained in 58.9% yield in substantially the same manner as that of Preparation 20-1)

NMR (CDCl₃, δ) : 1.60–1.70 (1H, m), 2.32–2.50 (1H, m), 2.85–3.30 (2H, m), 3.83–4.52 (5H, m), 4.62–4.66 (2H, m), 5.23–5.40 (2H, m), 5.86–6.06 (1H, m), 6.91 (1H, s), 7.08 (1H, s), 7.46 (1H, s)

Preparation 20-3)

(2S,4S)-4-Mercapto-1-(4-nitrobenzyloxycarbonyl)-2-(pyrazol-1-yl)methylpyrrolidine was obtained in 64.3% yield in substantially the same manner as that of Preparation 20-1).

IR (Neat): 1710–1690 cm⁻¹

NMR (CDCl₃, δ) : 5.25 (2H, s), 6.28 (1H, t, J=2.5Hz), 7.31 (1H, d, J=2.5Hz), 7.5–7.65 (3H, m), 8.27 (2H, d, J=8Hz)

Preparation 20-4)

(2S,4S)-4-Mercapto-1-(4-nitrobenzyloxycarbonyl)-2-(2-oxo-4-imidazolin-1-yl) methylpyrrolidine was obtained in 71.9% yield in substantially the same manner as that of Preparation 20-1).

IR (CH₂Cl₂) : 1700, 1690, 1520, 1340 cm⁻¹

NMR (CDCl₃, δ) : 1.60–2.04 (2H, m), 2.34–2.78 (1H, m), 3.00–3.53 (2H, m), 3.78–4.52 (4H, m), 5.26 (2H, s), 6.03–6.17 (1H, m), 6.17–6.36 (1H, m), 7.57 (2H, d, J=9Hz), 8.17 (2H, d, J=9Hz), 10.22–10 73 (1H, br s)

EXAMPLE 1

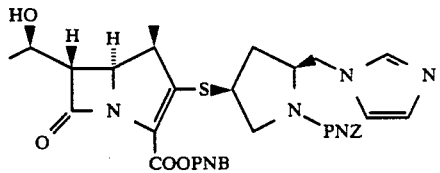

To a solution of 4-nitrobenzyl (4R)-2-diazo-4-[(2R,3S)-3-{(1R)-1-hydroxyethyl}-4-oxoazetidin-2-yl]-3-oxopentanoate (0.28 g) in 1.2-dichloroethane (15 ml) was added rhodium (II) acetate (2 mg) under reflux. The mixture was reluxed for 30 minutes under nitrogen atmosphere and concentrated under reduced pressure to give a syrup. The syrup was dissolved in acetonitrile (15 ml) and N,N-diisopropyl-N-ethylamine (0.37 ml). Diphenyl chlorophosphate (0.16 ml) was added thereto at −10−−5° C. in a nitrogen stream, followed by stirring at −10−−5° C. for 30 minutes. To the solution were added a solution of (2S,4S)-2-(imidazol-1-yl)methyl-4-mercapto-1-(4-nitrobenzyloxycarbonyl)pyrrolidine (0.26 g) in acetonitrile (2 ml) at −30−−25° C. and the mixture was stirred at 0–10° C. for 2 hours. The mixture was poured into ethyl acetate (75 ml), washed with water (50 ml ×2), dried over magnesium sulfate and concentrated under reduced pressure to give a syrup. The syrup was subjected to a column chromatography on sili ⓒa gel (20 g) and eluted with a mixture of acetone and dichloromethane (50:50, V/V) to give 4-nitrobenzyl (4R,5S,6S)-6-[(1R)-1-hydroxyethyl]-3-[(2S,4S)-2-(imidazol-1-yl)methyl-1-(4-nitrobenzyloxycarbonyl)-pyrrolidin-4-yl]thio-4-methyl -7-oxo-1-azabicyclo[3.2.0]-hept-2-ene-2-carboxylate (0.19 g).

IR (CHCl₃): 1770, 1705 cm⁻¹

NMR (CDCl₃ δ) : 6.80 (1H, s), 7.00 (1H, s)

EXAMPLE 2

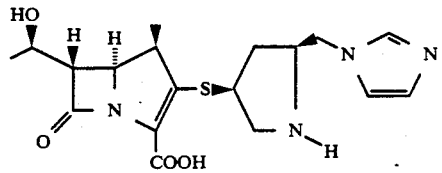

A solution of 4-nitrobenzyl (4R,5S,6)-6-[(1R)-1-hydroxyethyl]-3-[(2S,4S) -2-(imidazol-1-yl)methyl-1-(4-nitroenzyloxycarbonyl)pyrrolidin-4-yl]thio-4-methyl-7-oxo-1-azabicyclo-3.2.0]hept-2-ene-2-carboxylate (0.18 g) in a mixture of tetrahydrofuran (20 ml) and 0.1 M phosphate buffer (PH 6.5) (20 ml) was stirred in the presence of 20% palladium hydroxide on carbon (0.05 g) under atmospheric pressure of hydrogen at ambient temperature for 5 hours. The catalyst was removed by filtration and the filtrate was concentrated under reduced pressure to remove the tetrahydrofuran. The residual solution was washed with ethyl acetate (20 ml ×2) and the organic solvent was removed by evaporation. The residual solution was subjected to a column chromatography on nonionic adsorption resin, "Diaion HP-20" (trademark, made by Mitsubishi Chemical Industries) (10 ml), washed with a mixture of acetone and water (2:98 V/V), and eluted with a mixture of acetone and water (5:95 V/V). The fractions containing the desired compound were collected and lyophilized to give (4R,5S,6S)-6-[(1R)-1-hydroxyethyl]-3-[(2S, 4S)-2-(imidazol-1-yl)-methylpyrrolidin-4-yl]thio-4-methyl-7-oxo-1-azabicyclo[3.2.0]-hept -2-ene-2-carboxylic aicd (0.079 g).

mp : 170° C. (dec.)

IR (KBr) : 1750 cm$^{-1}$

NMR (D$_2$O, δ) : 1.20 (3H, d, J=7Hz), 1.28 (3H, d, J=7Hz), 7.19 (1H, s), 7.30 (1H, s), 8.07 (1H, s)

SIMS, 391 (M+−1), 347 (M+−45)

EXAMPLE 3-1

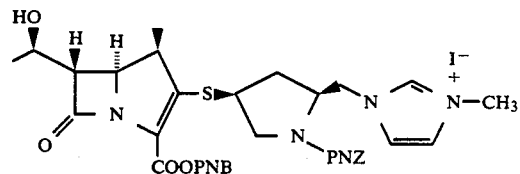

To a solution of 4-nitrobenzyl (4R,5S,6S)-6-[(1R)-1-hydroxyethyl]-3-[(2S,4S) -2-(imidazol-1-yl)methyl-1-(4-nitrobenzyloxycarbonyl)pyrrolidin-4-yl]thio-4-methyl-7-oxo-1-azabicyclo[3.2.0]hept-2-ene-2-carboxylate (0.61 g) in tetrahydrofuran (3 ml) was added methyl iodide (2 ml) and stirred at ambient temperature for 15 hours. The mixture was concentrated under reduced pressure to give crude 4-nitrobenzyl (4R,5S,6S)-6-[(1R)-1-hydroxyethyl]-4-methyl-3-[(2S,4S)-2-(3-methyl-1-imidazolio)methyl-1-(4-nitrobenzyloxycarbonyl) pyrrolidin-4-yl]thio-7-oxo-1-azabicyclo[3.2.0]hept-2-ene-2-carboxylate iodide (0.80 g).

IR (Nujol) : 1760, 1705–1685 cm$^{-1}$

EXAMPLE 3-2

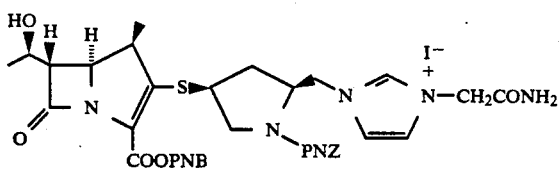

A solution of 4-nitrobenzyl (4R,5S,6S)-6-[(1R)-1hydroxyethyl]-3- [2S,4S)-2-(imidazol-1-yl)methyl-1-(4-nitrobenzyloxycarbonyl)pyrrolidin-4-yl]thio-4-methyl-7-oxo-1-azabicyclo [3.2.9]hept-2-ene-2-carboxylate (0.80 g) and iodoacetamide (0.62 g) in acetonitrile (16 ml) was stirred at ambient temperature for 60 hours. The mixture was concentrated under reduced pressure to give crude 4-nitrobenzyl (4R,5S,6S)-3-[(2S,4S)--2-(3-carbamoylmethyl-1-imidazolio)methyl-1-(4-nitrobenzyloxycarbonyl)pyrrolidin-4-yl]thio-6-[(1R)-1-hydroxyethyl]-4-methyl-7-oxo-1azabicyclo[3.2.0]hept-2-ene-2-carboxylate iodide (1.44 g).

IR (CHCl$_3$) 1760, 1710–1655 cm$^{-1}$

EXAMPLE 3-3

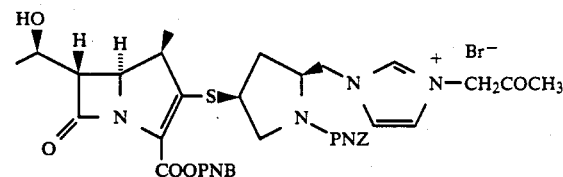

A solution of 4-nitrobenzyl (4R,5S,6S)-6-[(1R)-1hydroxyethyl]-3-[(2S,4S)-2(imidazol-1-yl)methyl-1-(4-nitrobenzyloxycarbonyl)pyrrolidin-4-yl]thio-4-methyl-7-oxo1- azabicyclo [3.2.0]hept-2-ene-2-carboxylate (0.80 g) and bromoacetone (0.3 ml) in tetrahydrofuran (8 ml) was stirred at ambient temperature for 18 hours. The mixture was concentrated under reduced pressure to give crude 4-nitrobenzyl (4R,5S,6S)-3-[(2-S,4S)-2-(3-acetonyl-1-imidazolio)-methyl-1-(4-nitrobenzyloxycarbonyl)pyrrolidin-4-yl]thio-6-[(1R)-1-hydroxyethyl]-4-methyl-7-oxo-1-azabicyclo[3.2.0]hept-2-ene-2-carboxylate bromide (1.20 g).

IR (Neat) : 1765–1690 cm$^{-1}$

EXAMPLE 3-4)

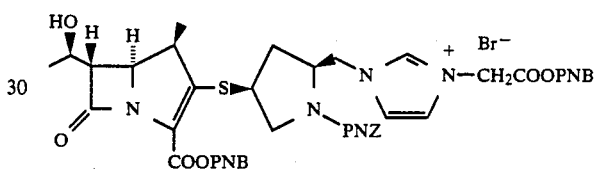

A solution of 4-nitrobenzyl (4R,5S,6S)-6-[(1R)-1hydroxyethyl]-3-[(2S,4S) -2-(imidazol-1-yl)methyl-1-(4-nitrobenzyloxycarbonyl)pyrrolidin-4-yl]thio-4-methyl-7-oxo-1azabicyclo[3.2.0]hetp-2-ene-2-carboxylate (0.80g) and 4-nitrobenzyl bromoacetate (0.62 g) in tetrahydrofuran (8 ml) was stirred at ambient temperature for 80 hours. The mixture was concentrated under reduced pressure to give crude 4-nitrobenzyl (4R,5S,6S)-6-[(1R)-1-hydroxyethyl]-4-methyl-3-(2S,4S)-2-(3.(4-nitrobenzyloxycarbonyl)methyl-1-imidazolio]-methyl-1-(4-nitrobenzyloxycarbonyl)pyrrolidin-4-yl]thio-7-oxo-1-azabicyclo[3.2.0]hpet-2-ene-2-carboxylate bromide (1.45 g).

IR (Neat) : 1760–1740, 1710–1690 cm$^{-1}$

EXAMPLE 4-1)

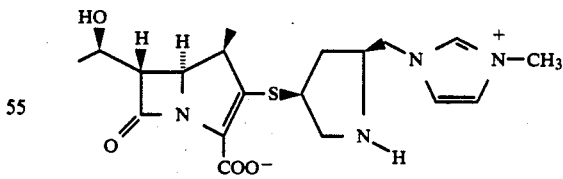

A solution of 4-nitrobenzyl (4R,5S,6S)-6-[(1R)-1-hydroxyethyl]-4-methyl-3-[(2S, 4S)-2-(3-methyl-1-imidazolio)methyl-1-4-nitrobenzyloxycarbonyl)pyrrolidin-4-yl]thio-7-oxo -1-azabicyclo-3.2.0]hept-2-ene-2-carboxylate iodide (0.79 g) obtained in Example 3-1) in a mixture of tetrahydrofuran (50 ml) and 0.1 M phosphate buffer (pH 6.5) (50 ml) was stirred in the presence of 20 % palladium hydroxide on carbon (0.3 g) under atmospheric pressure of hydrogen at ambient temperature for 5 hours. The catalyst was removed by filtration and the filtrate was concentrated under reduced pressure to remove the tetrahydrofuran. The residual solution was washed with ethyl acetate (50 ml ×2) and the organic solvent was removed by evaporation. The equeous solution was subjected to a column chromatography on nonionic adsorption resin, "Diaion HP-20" (50 ml), washed with water, eluted with a mixture of acetone and water (1:99 V/V). The fractionscontaining the desired compound were collected and lyophilized to give (4R,5S,6S)-6-[(1R)-1-hydroxyethyl]4-methyl-3-[(2S,4S)-2-(3-[(2S,4S)-2-(3-methyl-1-imidazolio)methyl-pyrrolidin-4-yl]thio-7-oxo-1-azabicyclo [3.2.0]hept-2-ene-2-carboxylate (0.25 g).

mp : 165° C. (dec.)
IR (KBr) : 1750–1730, 1590–1560 cm$^{-1}$
NMR (D$_2$O, δ) : 1.21 (3H, d, J=7Hz), 1.28 (3H, d, J=7Hz), 3.90 (3H, s), 7.46 (1H, s), 7.53 (1H, s), 8.80 (1H, s)
MS : 407

EXAMPLE 4-2)

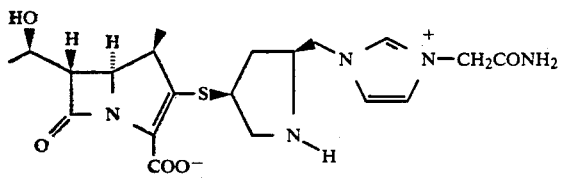

(4R,5S,6S)-3-[(2S,4S)-2-(3-Carbamoylmethyl-1-imidazolio)-methylpyrrolidin-4-yl]thio-6-[(1R)-1-hydroxyethyl]-4-methyl-7-oxo-1-azabicyclo[3.2.0]hept-2-ene-2-carboxylate was obtained in substantially the same manner as that of Example 4-1) in 74.5 % yield based on 4-nitrobenzyl (4R,5S,6S)-6-[(1R)-1hydroxyethyl]-3-[(2S, 4S)-2-(imidazol-1-yl)methyl-1-(4-nitrobenzyloxycarbonyl)pyrrolidin-4-yl]thio-4-methyl-7-oxo-1-azabicyclo[3.2.0]hept-2-ene-2-carboxylate.

mp : 175° C. (dec.)
IR (KBr) : 1750–1730, 1690–1680 cm$^{-1}$ 5.11 (2H, s), 7.55 (1H, d, J=2Hz), 7.65 (1H, d, J=2Hz)
MS : 450 (M 1)

EAMPLE 4-3)

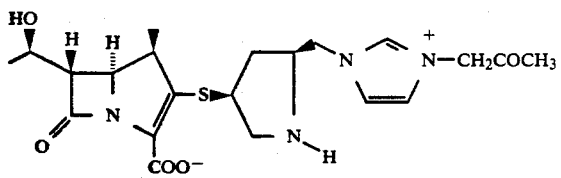

(4R,5S,6S)-3-[(2S,4S)-2-(3-Acetonyl-1-imidazolio)-methylpyrrolidin-4-yl]thio -6-[(1R)-1-hydroxyethyl]-4-methyl-7-oxo-1-azabicyclo[3.2.0]hept-2-ene-2-carboxylaate was obtained in substantially the same manner as that of Example 4-1) in 59.0 % yield based on 4-nitrobenzyl (4R,5S,6S)-6-[(1R)-1hydroxyethyl]-3-[(2S, 4S)-2-(imidazol-1-yl)methyl-1-(4-nitrobenzyloxycarbonyl)-pyrrolidin-4-yl]thio-4-methyl-7-oxo -1-azabicyclo[3.2.0-]hept-2-ene-2-carboxylate.

mp : 195° C. (dec.)
IR (KBr) : 1750–1720 cm$^{-1}$
NMR (D$_2$O, δ) : 1.21 (3H, d, J=7Hz), 1.28 (3H, d, J=7Hz), 2.33 (3H, s), 7.38 (1H, d, J=2Hz), 7.56 (1H, d, J=2Hz),
MS : 449 (M+1)

EXAMPLE 4-4)

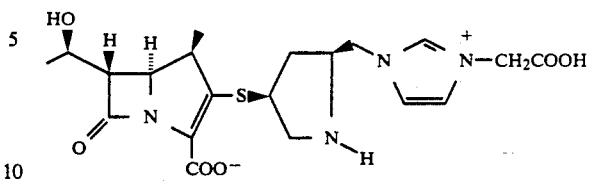

(4R,5S,6S)-3-[(2S,4S)-2-(3-Carboxymethyl-1-imidazolio)methylpyrrolidin-4-yl]thio-6-[(1R)-1-hydroxyetyl]-4-methyl-7-oxo-1-azabicyclo[3.2.0]hept-2-ene-2-carboxylate was obtained in 68.6 % yield in substantially the same manner as that of Example 4-1) based on 4-nitrobenzyl (4R,5S,6S)-6-[(1R)-1-hydroxyethyl]-3-[(2S,4S)-2-(imidazol-1-yl)methyl-1-(4-nitrobenzyloxycarbonyl)pyrrolidin-4-yl]thio-4-methyl -7-oxo-1-azabicyclo[3.2.0]hept-2-ene-2-carboxylate mp : 195° C. (dec.)
IR (KBr) : 1755–1725 cm$^{-1}$
NMR (D$_2$O, δ) : 1.21 (3H, d, J=7Hz), 1.28 (3H, d, J=7Hz), 7.51 (1H, br. s), 7.59 (1H, br. s), 8.91 (1H, s)
MS 451 (M$^+$+1)

EXAMPLE 5-1)

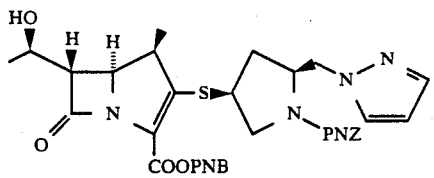

4-Nitrobenzyl (4R,5S,6S)-6-[(1R)-1-hydroxyethyl]-4-methyl-3-[(2S,4S) -1-(4-nitrobenzyloxycarbonyl)-2-(pyrazol-1-yl)methylpyrrolidin-4-yl]thio-7-oxo-1azabicyclo[3.2.0]hept-2-ene-2-carboxylate was obtained in 61.6 % yield in substantially the same manner as that of Example 1.

IR (CHCl$_3$) : 1765, 1710–1695 cm$^{-1}$

EXAMPLE 5-2)

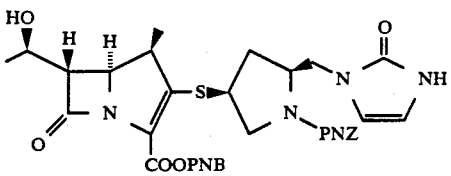

4-Nitrobenzyl (4R,5S,6S)-6-[(1R)-1-hydroxyethyl]-4-methyl-3-[(2S,4S) -1-(4-nitroenzyloxycarbonyl)-2-(2-oxo-4-imidazolin-1-yl)methylpyrrolidin-4-yl]thio-7-oxo -1-azabicyclo[3.2.0]hept-2-ene-2-carboxylate was otained in 65.1 % yield in substantially the same manner as that of Example 1.

IR (CH 1770, 1700, 1690, 1603, 1520, 1340 cm$^{-1}$
NMR (CDCl$_3$, δ) : 1.04–1.48 (6H, m), 1.70–2.67 (2H, m), 3.02–3.40 (1H, m), 3.73–4.47 (3H, m), 4.91–5 57 (4H, m), 5.90–6.27 (2H, m) 7.50 (2H, d, J=9Hz), 7.59 (2H, d, J=9Hz), 8.15 (4H, d, J=9Hz)

EXAMPLE 6-1)

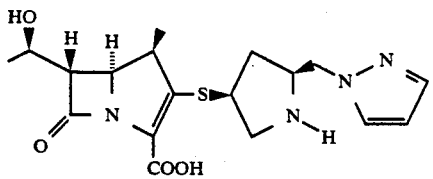

(4R,5S,6S)-6-[(1R)-1-Hydroxyethyl]-4-methyl-7-oxo-3-[(2S,4S) -2-(pyrazol-1-yl)methylpyrrolidin-4-yl]thio-1-azabicyclo[3.2.0]hept-2-ene-2-carboxylic acid was obtained in 63.6% yield in substantially the same manner as that of Example 2.

mp : 170° C. (dec.)
IR (KBr) : 1750-1700 cm$^{-1}$
NMR (D$_2$O, δ) : 1.20 (3H, d, J=7Hz), 1.28 (3H, d, J=7Hz), 6.38 (1H, t, J=2.5Hz), 7.63 (1H, d, J=2.5Hz), 7.75 (1H, d, J=2.5Hz)
SIMS : 393 (M$^+$+1), 307

EXAMPLE 6-2)

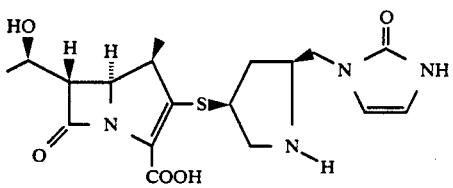

(4R,5S,6S)-6-[(1R)-1-Hydroxyethyl]-4-methyl-7-oxo-3-[(2S,4S) -2-(2-oxo-4-imidazolin-1-yl)methylpyrrolidin-4-yl]thio-1-azabicyclo[3.2.0]hept-2-ene -2-carboxylic acid was obtained in 60.7% yield in substantially the same manner as that of Example 2.

IR (Nujol) : 1760, 1660, 1460, 1380 cm$^{31\ 1}$
NMR (CDCl$_3$, δ) : 1.22 (3H, d, J=8Hz), 1.30 (3H, d, J=6Hz), 1.38-2.05 (2H, m), 2.44-2.90 (2H, m), 3.07-3.73 (4H, m), 3.73-4.33 (4H, m), 6.51 (2H, s)

EXAMPLE 7

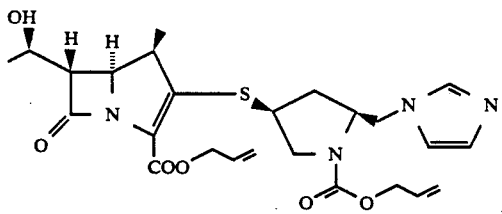

To a solution of allyl (4R)-2-diazo-4-[(2R,3S)-3-{(1R)-1-hydroxyethyl}-4-oxoazetidin-2-yl]-3-oxopentanoate (16.0 g) in ethyl acetate (160 ml) was added rhodium(II) octanoate (0.21 g) under refluxing in a stream of nitrogen. The mixture was refluxed for 30 minutes and evaporated in vacuo to give a residue. The residue was dissolved in acetonitrile (160 ml) and cooled to 0-5° C. under atmosphere of nitrogen. To the solution was added diphenyl chlorophosphate (12.4 ml) and N,N-diisopropyl-N-ethylamine (10.4 ml) successively and the mixture was stirred at the same condition for 2 hours and then stirred at ambient temperature for 2 hours. After cooling to 0-5° C., to the reaction mixture were added a solution of S,4S)-1-allyloxycarbonyl-2-(imidaZol-1-yl)methyl-4-mercaptopyrrolidine (17.15 g) in acetonitrile (80 ml) and N,N-diisopropyl-N-ethylamine (12.3 ml) successively. The mixture was stirred at 0-5° C. for 2 hours. To the mixture was added ethyl acetate (500 ml) and the solution was washed 3 times with saturated aqueous sodium chloride, dried over anhydrous magnesium sulfate and evaporated in vacuo. The resulting residue was chromatographed on silica gel (400 g) eluting with a mixture of dichloromethane and methanol (19:1, V/V). The fractions containing the desired compound were collected and evaporated in vacuo to give allyl (4R,5S,6S)-3-[(2S,4S)-1-allyloxycarbonyl-2-(imidazol -1-yl)methylpyrrolidin-4-yl]-thio-6-[(1R)-1-hydroxyethyl]-4-methyl-7-oxo-1-azabicyclo -[3.2.0]hept-2-ene-2-carboxylate (14.41 g).

IR (Neat) : 1760, 1705 (sh), 1690 cm$^{-1}$
NMR (CDCl$_3$, δ) : 1.22 (3H, d, J=7Hz), 1.32 (3H, d, J=6Hz), 1.47-1.88 (1H, m), 2.21-2.62 (1H, m), 2.90-3.40 (4H, m), 3.41-3.79 (1H, m), 3.85-4.46 (6H, m), 4.53-4.84 (4H, m), 5.12-5.56 (4H, m), 5.71-6.22 (2H, m), 6.89 (1H, s), 7.03 (1H, s), 7.46 (1H, s)

EXAMPLE 8-1)

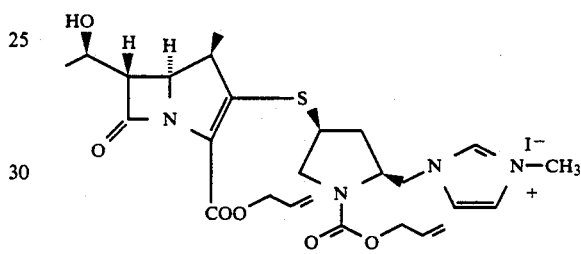

A mixture of allyl (4R,5S,6S)-3-[(2S,4S)-1-allyloxycarbonyl-2-(imidazol-1-yl) methylpyrrolidin-4-yl]thio-6-[(1R)-1-hydroxyethyl]-4-methyl-7-oxo-1-azabicyclo[3.2.0]-hept-2-ene-2-carboxylate (15.4 g), methyl iodide (18.6 ml) and acetone (80 ml) was stirred at ambient temperature for hours. The reaction mixture was evaporated in vacuo. The resulting residue was chromatographed on silica gel (75 g) eluting with a mixture of dichloromethane and methanol (9:1, V/V). The fractions containing the desired compound were collected and evaporated in vacu to give allyl (4R,5S,6S)-3-[(2S,4S)-1-allyloxycarbonyl-2-(3-methyl-1-imidazolio) methylpyrrolidin-4-yl]thio-6-[(1R)-1-hydroxyethyl]-4-methyl-7-oxo-1-azabicyclo[3.2.0]hept-2-ene-2-carboxylate iodide (17.72 g).

NMR (DMSO-d$_6$, δ) : 1.15 (6H, d, J=6Hz), 1.52-1.81 (1H, m), 2.52-2.75 (1H, m), 3.07-3.55 (4H, m), 3.86 (3H, s), 3.93-4.80 (11H, m), 5.04-5.47 (4H, m), 5.74-6.00 (2H, m), 7.70 (2H, s), 9.14 (1H, s)

EXAMPLE 8-2)

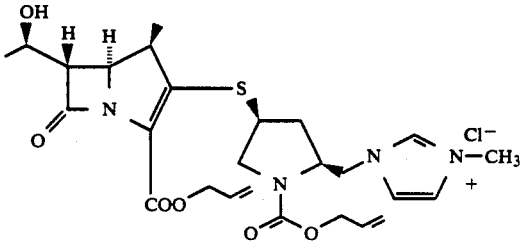

A mixture of allyl (4R,5S,6S)-3-[(2S,4S)-1-allyloxycarbonyl-2-(imidazol-1-yl)methyl pyrrolidin-4-yl]thio- 6-[(1R)-1-hydroxyethyl]-4-methyl-7-oxo-1azabicyclo[3.2.0]hept -2-ene-2-caroxylate (14.4 g), methyl iodide (17.4 ml) and acetone (140 ml) was stirred at ambient temperature overnight. The reaction mixture was evaporated in vacuo. The resulting residue was chromatographed on silica gel (300 g) eluting with a mixture of chloroform and methanol (9:1, V/V). The fractions containing the desired compound were collected and evaporated in vacuo. The resulting residue (14.93 g) was dissolved in a mixture of acetone (100 ml) and water (70 ml). The solution was passed through ion exchange resin, "Amberlist A-26" (Cl⁻_type, Trademark, made by Rohm and Haas CO., Ltd.) (300 ml) and eluted with a mixture of acetone (600 ml) and water (420 ml). The eluates were collected and evaporated in vacuo to remove the organic solvent. The resulting aqueous solution (100 ml) was lyophilized to give allyl (4R,5S,6S)-3-[(2S,4S)-1-allyloxycarbonyl-2-(3-methyl-1-imidazolio)methylpyrrolidin-4-yl]thio-6-[(1R)-1-hydroxyethyl]-4-methyl-7-oxo-1-azabicyclo[[3.2.0.-]hept-2-ene-2-carboxylate chloride (10.18 g).

This compound was immediately used as the atarting compound of Example 9-2).

EXMAPLE 9-1)

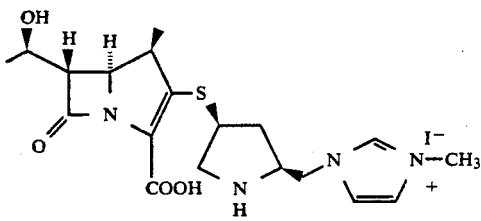

To a solution of allyl (4R,5S,6S)-3-[(2S,4S)-1-allyloxycarbonyl-2-(3-methyl-1-immidazolio)methylpyrrolidin-4-yl]thio-6-[(1R)-1-hydroxyethyl]-4-methyl-7-oxo-1azabicyclo[[3.2.0]hept-2-ene-2-carboxylate iodide (2.0 g), triphenylphosphine (80 mg) and morpholine (0.79 ml) in a mixture of tetrahydrofuran (10 ml), ethanol (20 ml) and water (2 ml) was added tetrakis(triphenylphosphine)palladium(0) (70 mg) at ambient temperature in a stream of nitrogen. The mixture was stirred at the same condition for 3 hours. The resulting precipitates were collected by filtration, washed with tetrahydrofuran and dried in vacuo at 40° C. for 4 hours to give (4R,5S,6S)-6-[(1R)-1-hydroxyethyl]-4-methyl-3-[(2S,4S)-2-(3-methyl-1-imidazolio)methylpyrrolidin-4-yl]thio-7-oxo-1-azabicyclo-[3.2. 0]hpet-2-ene-2-carboxylic acid iodide (0.90 g).

IR (Nujol) : 1760, 1600, 1530, 1220, 1170 cm⁻¹

NMR (D₂O) : 1.23 (3H, d, J=7Hz), 1.29 (3H, d, J=6Hz), 1.63-2.06 (1H, m), 2.66-3.04 (1H, m), 3.26-3.86 (4H, m), 3.94 (3H, s), 3.96-4.43 (4H, m), 7.52-7.70 (2H, m), 8.93 (1H, broad s)

EXAMPLE 9-2)

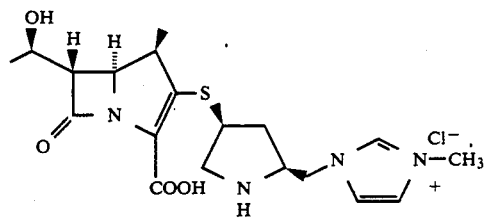

To a solution of allyl (4R,5S,6S)-3-[(2S,4S)-1-allyloxycarbonyl-2-(3-methyl-1-imidazolio)methylpyrrolidin-4-yl]thio-6-[(1R)-1-hydroxyethyl]-4-methyl-7-oxo-1-azabicyclo[3.2.0]hept-2-ene-2-carboxylate chloride (0.5 g), triphenylphosphine (23 mg) and N-methylpiperazine (0.29 ml) in a mixture of tetrahydrofuran (6 ml), ethanol (12 ml) and water (0.5 ml) was added tetrakis(triphenylphosphine)palladium(0) (20.4 mg) at ambient temperature with stirring. The mixture was stirred at the same temperature for 1 hour. The reaction mixture was adjusted to pH 6 with conc. hydrochloric acid and the mixture was evaporated in vacuo to remove the organic solvent. The resulting aqueous solution (10 ml) was washed with ethyl acetate (10 ml) and chromatographed on nonionic adsorption resin, "Diaion HP-20" (20 ml) eluting in turn with water (40 ml) and 3% aqueous acetone (80 ml). The fractions containing the desired compound ware collected and evaporated in vacuo. The resulting residue (10 ml) was adjusted to pH 3.5 with 1N hydrochloric acid and the solution was passed through ion exchange resin, "Amberlist A-26" (10 ml) and eluted with water (30 ml). The eluate was evaporated in vacuo to give a residue. The residue was dissolved in ethanol (50 ml) and the solution was stirred under ice-cooling for 1 hour. The resulting crystals were collected by filtration and dried in vacuo to give (4R,5S,6S)-6-[(1R)-1-hydroxyethyl]-4-methyl-3-[(2S,4S)-2-(3-methyl-1-imidazolio)methylpyrrolidin-4-yl]thio-7-oxo-1-azabicyclo[3.2.0]hept-2-ene-2-carboxylic acid chloride (0.17 g).

mp : >176° C. (dec.)

IR (Nujol) : 1755, 1600, 1560, 1530, 1265, 1240, 1170 cm⁻¹

NMR (D₂O, δ) : 1.20 (3H, d, J=7Hz), 1.27 (3H, d, J=6Hz), 1.56-2.05 (2H, m), 2.60-3.03 (1H, m), 3.92 (3H, s), 7.56 (2H, m), 8.88 (1H, broad s)

Elemental Analysis:
Calculated (%) : Cl 8.00, I 0;
Found (%) Cl 7.92 I<0.005.

EXAMPLE 10

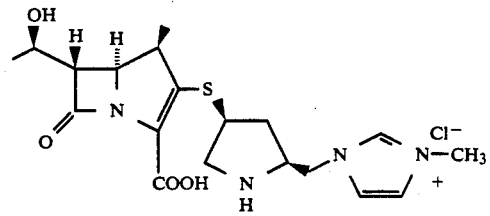

A solution of (4R,5S,6S)-6-[(1R)-1-hydroxyethyl]-4-methyl-3-[(2S,4S) -2-(3-methyl-1-imidazolio)methylpyrrolidin-4-yl]thio-7-oxo-1-azabicyclo[3.2.0]hept-2-ene-2-carboxylate iodide (3.07 g) in water (60 ml) was passed through ion exchange resin, "Amberlist A-26" (15 ml) and eluted with water (120 ml). The eluate was evaporated in vacuo to give a residue. The residue (7.91 g) was dissolved in ethanol (60 ml) and the solution was stirred under ice-cooling for 1 hour. The resulting precipitates were collected by filtration, washed with stirred under ice-cooling for 1 hour. The resulting precipitates were collected by filtration, washed with acetone (30 ml) and dried in vacuo to give (4R,5S,6S)-6-[(1R)-1-hydroxyethyl]-4-methyl -3-[(2S,4S)-2-(3-methyl-1-imidazolio)methylpyrrolidin-4-yl]thio-7-oxo-1-azabicyclo[3.2.0]hept-2-ene-2-carboxylic acid chloride (1.57 g).

IR (Nujol) : 1755, 1600, 1560, 1530, 1265, 1240, 1170 cm$^{-1}$

NMR (D$_2$O, δ) : 1.20 (3H, d, J=7Hz), 1.27 (3H, d, J=6Hz), 1.56–2.05 (2H, m), 2.60–3.03 (1H, m), 3.92 (3H, s), 7.56 (2H, m), 8.88 (1H, broad s)

EXAMPLE 11

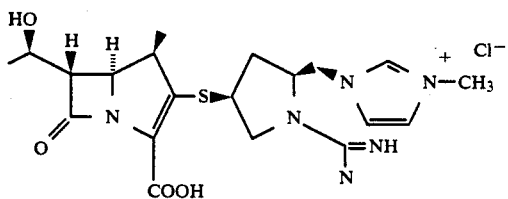

To a solution of (4R,5S,6S)-6-[(1R)-1-hydroxyethyl]-4-methyl-3-[(2S,4S) -2-(3-methyl-1-imidazolio)methylpyrrolidin-4-yl]thio-7-oxo-1-azabicyclo[3.2.0]hept-2-ene 2-carboxylate chloride (270 mg) in water (6 ml) was added a solution of benzyl formimidate hydrochloride (330 mg) in water 3 ml) at 0° C., keeping the pH between 8.0–8.5 with 4N aqueous sodium hydroxide. After stirring for 3 hours, pH of the reaction mixture was adjusted to 6.7 with 1N hydrochloric acid. The mixture was washed with ethyl acetate (20 ml ×3) and the aqueous layer was separated, concentrated in vacuo to give a residual solution, which was chromatographed on "Diaion HP-20" eluting in turn with water and a mixture of acetone and water (1:50-1:20 V/V). The fractions containing the desired compound were collected and lyophilized to give (4R,5S,6S)-6-[(1R)-1-hydroxyethyl]-4-methyl-3-[(2S,4S)-1-formimidoyl-2-(3-methyl-1-imidazolio)methylpyrrolidin-4-yl]thio-7-oxo-1-azabicyclo[3.2.0]hept-2-ene-2-carboxylic acid chloride (90 mg).

IR (Nujol) : 3100–3400, 1700–1740, 1635–1675, 1560–1610 cm$^{-1}$

NMR (D$_2$O, δ) : 1.03 (3H, d, J=7Hz), 1.24 (3H, d, J=7Hz), 2.20 (3H, s), 7.36–7.50 (2H, m), 7 67–7.88 (1H, m), 8.06 (1H, s), 8.65–8.82 (1H, m).

What we claim is:

1. A compound of the formula which is selected from the group consisting of the formula:

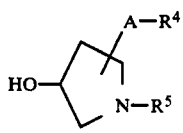

the formula:

-continued

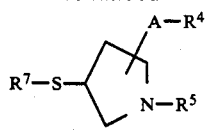

and the formula:

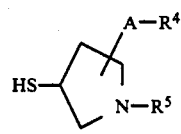

in which $R^4$ is a heterocyclic group selected from the group consisting of pyrrolyl, pyrrolinyl, imidazolyl, imidazolinyl, pyrazolyl, pyrazolinyl, pyridyl, pyridyl N-oxide, pyridinio, dihydropyridyl, tetrahydropyridyl, pyrimidinyl, pyrimidinio, pyrazinyl, pyrazinio, pyridazinyl, pyridazinio, triazinyl, tetrahydrotriazinyl, triazinio, triazolyl, triazolio, tetrazinyl, tetrazinio, tetrazolyl and tetrazolio wherein said heterocyclic group may be substituted by one to three substituent(s) selected from a group consisting of oxo, carboxy(lower)alkyl, protected carboxy(lower)alkyl, amino protected amino, lower alkylamino, ureido(lower)alkyl, carbamoyl, carbamoyl(lower)alkyl, lower alkyl, lower alkanoyl(lower)alkyl, amino(lower)alkyl, protected amino(lower)alkyl, hydroxy(lower)alkyl, protected hydroxy(lower)alkyl, azido(lower)alkyl, halo(lower)alkyl and imino-protective group, $R^5$ is hydrogen, lower alkanimidoyl or imino-protective group, $R^7$ is ar(lower)alkyl or acyl derived from a carboxylic, carbonic, sulfonic or carbamic acid, and A is lower alkylene, or a salt thereof.

2. The compound of claim 1, wherein said heterocyclic group may be substituted by one to three substituent(s) selected from a group consisting of oxo, carboxy(lower)alkyl, protected carboxy(lower)alkyl, amino, protected amino, lower alkylamino, ureido(lower)alkyl, carbamoyl, carbamoyl(lower)alkyl, lower alkyl, lower alkanoyl(lower)alkyl, amino(lower)alkyl, protected amino(lower)alkyl, hydroxy(lower)alkyl, protected hydroxy(lower)alkyl, azido(lower)alkyl, halo(lower)alkyl and aliphatic acyl or aliphatic acyl substituted with aromatic group(s), said acyl optionally being substituted with nitro, $R^5$ is hydrogen, lower alkanimidoyl, aliphatic acyl or aliphatic acyl substituted with aromatic group(s); said acyl optionally being substituted with nitro, and $R^7$ is ar(lower)alkyl, aliphatic acyl or aliphatic acyl substituted with aromatic group(s), said acyl optionally being substituted with nitro.

3. The compound of claim 1, wherein $R^4$ is imidazolyl, pyrazolyl or imidazolinyl, said heterocyclic group being substituted or unsubstituted by a group consisting of oxo, carboxy(lower)alkyl, lower alkenyloxcarbonyl(lower)alkyl, phenyl (or nitrophenyl)(lower)alkyl, lower alkanoyloxy(lower)alkyl, lower alkenyloxycarbonyl or phenyl (or nitrophenyl)(lower)alkoxycarbonyl, and $R^5$ is hydrogen, lower alkanimidoyl, lower alkenyloxycarbonyl or phenyl (or nitrophenyl)(lower)alkoxycarbonyl.

4. The compound of claim 3, wherein
$R^4$ is imidazolyl, pyrazolyl, imidazolinyl or oxoimidazolinyl, and
$R^5$ is hydrogen or lower alkanimidoyl.

5. The compound of claim 4, wherein
$R^4$ is imidazolyl, pyrazolyl, imidazolin-1-yl or 2-oxoimidazolin-1-yl,
$R^5$ is hydrogen or $C_1$–$C_4$ alkanimidoyl, and
A is $C_1$–$C_4$ alkylene.

6. The compound of claim 5, wherein
$R^4$ is imidazol-1-yl, pyrazol-1-yl, imidazolin-1-yl or 2-oxoimidazolin-1-yl,
$R^5$ is hydrogen or formimidoyl, and
A is methylene.

* * * * *

UNITED STATES PATENT AND TRADEMARK OFFICE
CERTIFICATE OF CORRECTION

PATENT NO. : 5,194,624

DATED : March 16, 1993

INVENTOR(S) : Masayoshi Murata et al.

It is certified that error appears in the above-identified patent and that said Letters Patent is hereby corrected as shown below:

On the title page, Item [75],

The second inventor's name is spelled incorrectly, should be,

--Hideo Tsutsumi--

Signed and Sealed this

Sixteenth Day of November, 1993

*Attest:*

BRUCE LEHMAN

*Attesting Officer*     *Commissioner of Patents and Trademarks*